(12) United States Patent
Isaacs et al.

(10) Patent No.: US 12,161,862 B2
(45) Date of Patent: *Dec. 10, 2024

(54) DEVICES AND METHODS FOR REPAIRING DAMAGE TO A TISSUE

(71) Applicants: BioCircuit Technologies, Inc., Atlanta, GA (US); Virginia Commonwealth University, Richmond, VA (US)

(72) Inventors: Jonathan Isaacs, Richmond, VA (US); Isaac Perry Clements, Marietta, GA (US); Andrew Willsie, Lilburn, GA (US); James David Ross, Decatur, GA (US); Alex Weidenbach, Atlanta, GA (US)

(73) Assignees: BioCircuit Technologies, Inc., Atlanta, GA (US); Virginia Commonwealth University, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/582,060

(22) Filed: Feb. 20, 2024

(65) Prior Publication Data

US 2024/0189583 A1  Jun. 13, 2024

Related U.S. Application Data

(63) Continuation of application No. 17/519,817, filed on Nov. 5, 2021, now Pat. No. 11,918,801, which is a
(Continued)

(51) Int. Cl.
*A61B 17/11* (2006.01)
*A61B 5/00* (2006.01)
(Continued)

(52) U.S. Cl.
CPC .............. *A61N 1/0556* (2013.01); *A61B 5/24* (2021.01); *A61B 5/388* (2021.01); *A61B 5/6877* (2013.01);
(Continued)

(58) Field of Classification Search
CPC ................ A61N 1/0556; A61N 1/0558; A61N 1/36103; A61B 5/6877; A61B 5/04001; A61B 5/6882
See application file for complete search history.

(56) References Cited

U.S. PATENT DOCUMENTS

| 3,123,077 A | 3/1964 | Alcamo |
| 4,461,304 A | 7/1984 | Kuperstein |

(Continued)

FOREIGN PATENT DOCUMENTS

| CA | 2816326 A1 | 5/2012 |
| WO | 2011091169 A1 | 7/2011 |

(Continued)

OTHER PUBLICATIONS

International Search Report and Written Opinion issued in related International Application No. PCT/US2017/050348 on Nov. 7, 2017 (8 pages).

(Continued)

*Primary Examiner* — Adam Z Minchella
(74) *Attorney, Agent, or Firm* — Meunier Carlin & Curfman LLC

(57) ABSTRACT

An example device for repairing a tissue is described herein. The device can include a flexible carrier layer, and a support member including a plurality of micro-protrusions extending therefrom. The support member can be at least partially integrated with the flexible carrier layer. Additionally, the flexible carrier layer can be configured to cover at least a portion of the tissue, and the micro-protrusions can be configured to mechanically interface with the tissue.

28 Claims, 16 Drawing Sheets

Related U.S. Application Data continuation of application No. 17/306,049, filed on May 3, 2021, now Pat. No. 11,167,131, which is a continuation of application No. 15/697,358, filed on Sep. 6, 2017, now Pat. No. 10,994,130.

(60) Provisional application No. 62/383,934, filed on Sep. 6, 2016.

(51) Int. Cl.
    *A61B 5/24*      (2021.01)
    *A61B 5/388*     (2021.01)
    *A61N 1/05*      (2006.01)
    *A61N 1/36*      (2006.01)

(52) U.S. Cl.
    CPC .......... *A61B 5/6882* (2013.01); *A61N 1/0558* (2013.01); *A61N 1/36103* (2013.01)

(56) References Cited

U.S. PATENT DOCUMENTS

| | | | |
|---|---|---|---|
| 4,586,504 A | 5/1986 | De Medinaceli | |
| 4,669,474 A | 6/1987 | Barrows | |
| 4,837,049 A | 6/1989 | Byers et al. | |
| 4,969,468 A | 11/1990 | Byers et al. | |
| 5,031,621 A | 7/1991 | Grandjean et al. | |
| 5,171,253 A | 12/1992 | Klieman | |
| 5,215,088 A | 6/1993 | Normann et al. | |
| 5,354,305 A | 10/1994 | Lewis, Jr. et al. | |
| 5,634,462 A | 6/1997 | Tyler | |
| 5,906,617 A | 5/1999 | Meislin | |
| 6,042,605 A | 3/2000 | Martin et al. | |
| 6,151,519 A | 11/2000 | Sugihara et al. | |
| 6,485,503 B2 | 11/2002 | Jacobs et al. | |
| 6,600,956 B2 | 7/2003 | Maschino et al. | |
| 6,645,226 B1 | 11/2003 | Jacobs et al. | |
| 6,690,959 B2 | 2/2004 | Thompson | |
| 6,745,062 B1 | 6/2004 | Finneran et al. | |
| 6,991,643 B2 | 1/2006 | Saadat | |
| 7,351,250 B2 | 4/2008 | Zamierowski | |
| 7,359,744 B2 | 4/2008 | Lee et al. | |
| 7,837,706 B2 | 11/2010 | Sogard et al. | |
| 8,359,083 B2 | 1/2013 | Clark et al. | |
| 8,588,884 B2 | 11/2013 | Hegde et al. | |
| 8,721,664 B2 | 5/2014 | Ruff et al. | |
| 8,747,437 B2 | 6/2014 | Leung et al. | |
| 8,781,576 B2 | 7/2014 | Savage et al. | |
| 8,858,577 B2 | 10/2014 | Kubiak | |
| 8,926,659 B2 | 1/2015 | Genova et al. | |
| 9,061,464 B2 | 6/2015 | Li et al. | |
| 9,149,496 B2 | 10/2015 | Matheny | |
| 9,173,583 B2 | 11/2015 | Chen et al. | |
| 9,248,273 B2 | 2/2016 | Guvanasen et al. | |
| 9,700,221 B2 | 7/2017 | Rajaraman et al. | |
| 9,980,834 B2 | 5/2018 | Brocker et al. | |
| 10,231,736 B2 | 3/2019 | Shah et al. | |
| 10,420,636 B2 | 9/2019 | Obermiller et al. | |
| 2002/0022861 A1* | 2/2002 | Jacobs .................. | A61B 17/064 606/213 |
| 2003/0023316 A1 | 1/2003 | Brown et al. | |
| 2004/0006264 A1 | 1/2004 | Mojarradi et al. | |
| 2005/0228409 A1 | 10/2005 | Coppi | |
| 2005/0277577 A1 | 12/2005 | Hunter et al. | |
| 2007/0191910 A1 | 8/2007 | Ren | |
| 2007/0282374 A1* | 12/2007 | Sogard ................ | A61B 17/0057 606/219 |
| 2008/0138581 A1 | 6/2008 | Bhandari et al. | |
| 2008/0138583 A1 | 6/2008 | Bhandari et al. | |
| 2010/0268055 A1 | 10/2010 | Jung et al. | |
| 2011/0147046 A1* | 6/2011 | Bonde .................. | A61N 1/0556 174/126.1 |
| 2011/0288566 A1 | 11/2011 | Kubiak | |
| 2011/0295100 A1 | 12/2011 | Hegde et al. | |
| 2013/0004559 A1 | 1/2013 | Li | |
| 2013/0253299 A1 | 9/2013 | Weber et al. | |
| 2014/0066958 A1 | 3/2014 | Priewe | |
| 2014/0107590 A1 | 4/2014 | Winograd et al. | |
| 2014/0148897 A1* | 5/2014 | Matheny ............... | A61F 2/848 623/1.36 |
| 2014/0163589 A1 | 6/2014 | Hoke et al. | |
| 2014/0205792 A1 | 7/2014 | Anderson | |
| 2014/0228738 A1 | 8/2014 | Park et al. | |
| 2014/0336487 A1 | 11/2014 | Wang et al. | |
| 2015/0066064 A1 | 3/2015 | Kubiak | |
| 2015/0359933 A1 | 12/2015 | Matheny | |
| 2016/0100933 A1 | 4/2016 | Linder et al. | |
| 2016/0143729 A1 | 5/2016 | Matheny | |
| 2017/0172437 A1 | 6/2017 | Butera et al. | |

FOREIGN PATENT DOCUMENTS

| | | |
|---|---|---|
| WO | 2013188884 A1 | 12/2013 |
| WO | 2016085513 A1 | 6/2016 |
| WO | 2017151806 A1 | 9/2017 |

OTHER PUBLICATIONS

Evans et al., "Selective reinnervation: A comparison of recovery following micro suture and conduit nerve repair," Brain Res., 1991;559(2):315-321.

Lundborg et al., "Tubular repair of the median or ulnar nerve in the human forearm: a 5-year follow-up," Journal of hand surgery, 2004;29(2):100-107.

Ackermann, Jr., D.M., et al., "Effect of Nerve Cuff Electrode Geometry on Onset Response Firing in High-Frequency Nerve Conduction Block," IEEE Transactions on Neural Systems and Rehabilitation Engineering, vol. 18, No. 6, 2010, pp. 658-665.

Boger, A., et al., "Different clinical electrodes achieve similar electrical nerve conduction block," Journal of Neural Engineering, vol. 10, 2013, 9 pages.

Branner, A., et al., "A multielectrode array for intrafascicular recording and stimulation in sciatic nerve of cats," Brain Research Bulletin, vol. 51, No. 4, 2000, pp. 293-306.

Branner, A., et al., "Long-Term Stimulation and Recording With a Penetrating Microelectrode Array in Cat Sciatic Nerve," IEEE Transactions on Biomedical Engineering, vol. 51, No. 1, 2004, pp. 146-157.

Branner, A., et al., "Selective Stimulation of Cat Sciatic Nerve Using an Array of Varying-Length Microelectrodes," Journal of Neuropsychology, vol. 85, No. 4, 2001, pp. 1585-1594.

Fitzpatrick, D.M., et al., "A Nerve Cuff Design for the Selective Activation and Blocking of Myelinated Nerve Fibres," Neuromuscular Systems, Annual International Conference of the IEEE Engineering in Medicine and Biology Society, vol. 13, No. 2, 1991, pp. 906-907.

Harreby, K.R., et al., "Subchronic Stimulation Performance of Transverse Intrafascicular Multichannel Electrodes in the Median Nerve of the Göttingen Minipig," Artificial Organs, vol. 39, No. 2, Feb. 2015, pp. E36-E48.

Jellema, T., et al., "A Miniaturized Cuff Electrode for Electrical Stimulation of Peripheral Nerves in the Freely Moving Rat," Brain Research Bulletin, vol. 37, No. 6, 1995, pp. 551-554.

Korivi, N.S., et al., "Self-closing Cuff Electrode for Functional Neural Stimulation and Recording," Journal of Medical and Biological Engineering, vol. 31, No. 5, 2011, pp. 353-357.

Leventhal, D.K., et al., "Subfascicle Stimulation Selectivity Using a FINE," Proceedings of the 22nd Annual EMBS International Conference, 2000, 3 pages.

Loeb, G.E., et al., "Cuff electrodes for chronic stimulation and recording of peripheral nerve activity," Journal of Neuroscience Methods, vol. 64, 1996, pp. 95-103.

Malagodi, M.S., et al., "An Intrafascicular Electrode for Recording of Action Potentials in Peripheral Nerves," Annals of Biomedical Engineering, vol. 17, 1989, pp. 397-410.

Mathews, K.S., et al., "Assessment of Rat Sciatic Nerve Function Following Acute Implantation of High Density Utah Slanted Electrode Array (25 Electrodes/mm2) Based on Neural Recordings and Evoked Muscle Activity," Muscle & Nerve, Sep. 2014, pp. 417-424.

(56) References Cited

OTHER PUBLICATIONS

Naples, G.G., et al., "A Spiral Nerve Cuff Electrode for Peripheral Nerve Stimulation," IEEE Transactions on Biomedical Engineering, vol. 35, No. 1, 1988, pp. 905-916.
Navarro, X., et al., "A critical review of interfaces with the peripheral nervous system for the control of neuroprostheses and hybrid bionic systems," Journal of the Peripheral Nervous Systems, vol. 10, 2005, pp. 229-258.
Rousche, P.J., et al., "Chronic recording capability of the Utah Intracortical Electrode Array in cat sensory cortex," Journal of Neuroscience Methods, vol. 82, 1998, pp. 1-15.
Sahin, M., et al., "Improved Nerve Cuff Electrode Recordings with Subthreshold Anodic Currents," IEEE Transactions on Biomedical Engineering, vol. 45, No. 8, 1998, pp. 1044-1050.
Sweeney, J.D., et al., "A Nerve Cuff Technique for Selective Excitation of Peripheral Nerve Trunk Regions," IEEE Transactions on Biomedical Engineering, vol. 37, No. 7, 1990, pp. 706-715.
Taylor, J., et al., "Multiple-electrode nerve cuffs for low-velocity and velocity-selective neural recording," Medical and Biological Engineering Computing, vol. 42, 2004, pp. 634-643.
Tyler, D.J., et al., "A Slowly Penetrating Interfascicular Nerve Electrode for Selective Activation of Peripheral Nerves," IEEE Transactions on Rehabilitation Engineering, vol. 5, No. 1, 1997, pp. 51-61.
Tyler, D.J., et al., "Functionally Selective Peripheral Nerve Stimulation with a Flat Interface Nerve Electrode," IEEE Transactions on Neural Systems and Rehabilitation Engineering, vol. 10, No. 4, 2002, pp. 294-303.
Wang, K., et al., "Flexible Nerve Stimulation Electrode with Iridium Oxide Sputtered on Liquid Crystal Polymer," IEEE Transactions on Biomedical Engineering, vol. 56, No. 1, 2009, pp. 6-14.
Yoshida, K., et al., "Selective Stimulation of Peripheral Nerve Fibers using Dual Intrafascicular Electrodes," IEEE Transactions on Biomedical Engineering, vol. 40, No. 5, 1993, pp. 492-494.
Yu, H., et al., "A Parylene Self-Locking Cuff Electrode for Peripheral Nerve Stimulation and Recording," Journal of Microelectromechanical Systems, vol. 23, No. 5, Oct. 2014, pp. 1025-1035.
Alarcon, J., et al., "Preclinical Evaluation of Microneedle Technology for Intradermal Delivery of Influenza Vaccines," Clinical and Vaccine Immunology, 2007, vol. 14, No. 4, pp. 375-381.
Allen, D.M., "Photochemical Machining: from 'manufacturing's best kept secret' to a $6 billion per annum rapid manufacturing process," CIRP Annals—Manufacturing Technology, vol. 53, No. 2, 2004, pp. 559-572.
Bartels, J., et al., "Neurotrophic Electrode: Method of assembly and implantation into human speech cortex," Journal of Neuroscience Methods, vol. 174, No. 2, 2008, pp. 168-176.
Bhadra, N., et al., "High Frequency Electrical Conduction Block of Mammalian Peripheral Motor Nerve," Muscle Nerve, vol. 32, No. 6, 2005, pp. 782-790.
Blum, R. A., et al., "An Integrated System for Simultaneous, Multichannel Neuronal Stimulation and Recording," IEEE Transactions on Circuits and Systems I: Regular Papers, vol. 54, No. 12, 2007, pp. 2608-2618.
Bozon, J.P., et al., "Development of Metal-Based Microelectrode Sensor Platforms by Chemical Vapor Deposition," Electroanalysis, vol. 13, No. 11, 2001, pp. 911-916.
Brown, E.A., et al., "Stimulus-Artifact Elimination in a Multi-Electrode System," IEEE Transactions on Biomedical Circuits and Systems, vol. 2, No. 1, 2008, pp. 10-21.
Choi, S-O., et al, "An Electrically Active Microneedle Array for Electroporation of Skin for Gene Delivery," IEEE Transducers'05, 2005, pp. 1513-1516.
Davis, S.P., et al., "The Mechanics of Microneedles," Proceedings of the Second Joint EMBS/BMES Conferences, 2002, pp. 498-499.
Gill, H.S., et al., "Coated microneedles for transdermal delivery," Journal of Controlled Release, vol. 117, 2007, pp. 227-237.
Gill, H.S., et al., "Pocketed microneedles for drug delivery to the skin," Journal of Physics and Chemistry of Solids, vol. 69, 2008, pp. 1537-1541.
Griss, P., et al., "Characterization of Micromachined Spiked Biopotential Electrodes," IEEE Transactions on Biomedical Engineering, vol. 49, No. 6, 2002, pp. 597-604.
Griss, P., et al., "Micromachined Electrodes for Biopotential Measurements," IEEE Journal of MicroElectroMechanical Systems, vol. 10, No. 1, 2001, pp. 10-16.
Haq, M.I., et al., "Clinical administration of microneedles: skin puncture, pain and sensation," Biomed Microdevices, vol. 11, No. 1, 2009, pp. 35-47.
Hines, A.E., et al., "Stimulus artifact removal in EMG from muscles adjacent to stimulated muscles," Journal of Neuroscience Methods, vol. 64, No. 1, 1996, pp. 55-62.
Jobst, G., et al., "Thin-Film Micro-Biosensors for Glucose-Lactate Monitoring," Analytical Chemistry 68, 1996, pp. 3173-3179.
Joseph, L., et al., "High Frequency Stimulation Selectively Blocks Different Types of Fibers in Frog Sciatic Nerve," IEEE Trans. on Neural Systems and Rehabil Eng., vol. 19, No. 5, 2011, pp. 550-557.
Kaushik, S., et al., "Lack of Pain Associated with Microfabricated Microneedles," Anesth Analg, vol. 92, 2001, pp. 502-504.
Keller, O.C., et al. "Voltammetric and Reference Microelectrodes with Integrated Microchannels for Flow-Through Microvoltammetry. 2. Coupling the Microcell to a Supported Liquid Membrane Preconcentration Technique," Analytic Chemistry, vol. 72, 2000, pp. 943-948.
Kilgore, K.L., et al., "Nerve conduction block utilising high-frequency alternating current," Med. Biol. Eng. Comput., vol. 42, No. 3, 2004, pp. 394-406.
Knaflitz, M., et al., "Suppression of Simulation Artifacts from Myoelectric-Evoked Potential Recordings," IEEE Transactions on Biomedical Engineering, vol. 35, vol. 9, 1988, pp. 758-763.
Laurent, A., et al., "Echographic measurement of skin thickness in adults by high frequency ultrasound to assess the appropriate microneedle length for intradermal delivery of vaccines," Vaccine, vol. 25, 2007, pp. 6423-6430.
Lin, C.T., et al., "Noninvasive Neural Prostheses using Mobile and Wireless EEG," Proceedings of the IEEE, vol. 96, No. 7, 2008, pp. 1167-1183.
Martinez, A.W., et al., "Microfabrication and nanotechnology in stent design," WIREs Nanomedicine and Nanobiotechnology, vol. 3, 2011, pp. 256-268.
Matsumoto, T., et al., "Development of a micro-planar Ag/AgCl quasi-reference electrode with long-term stability for an amperometric glucose sensor," Analytica Chimica Acta, vol. 462, 2002, pp. 253-259.
Maurizio, I., et al., "Artifact Removal on surface EMG." Anno Accademico CCLXXIX, vol. XCIV, 2006, 9 pages.
McGill, K.C., et al., "On the Nature and Elimination of Stimulus Artifact in Nerve Signals Evoked and Recorded Using Surface Electrodes," IEEE Transactions on Biomedical Engineering, vol. BME-29, No. 2, 1982, pp. 129-137.
Merletti, R., et al., "Electrically Evoked Myoelectric Signals," Critical Reviews in Biomedical Engineering, vol. 19, No. 4, 1992, pp. 293-340.
Merletti, R., et al., "The linear electrode array: a useful tool with many applications," Journal of Electromyography and Kinesiology, vol. 13, No. 1, 2003, pp. 37-47.
Mezzi, A., et al., "Micro-chemical surface investigation of brittle carthaginian and roman silver artefacts," Surface and Interface Analysis, vol. 44, 2012, pp. 972-976.
Mikszta, J.A., et al., "Improved genetic immunization via micromechanical disruption of skin-barrier function and targeted epidermal delivery," Nature Medicine, vol. 8, 2002, pp. 415-419.
Minzly, J., et al., "Stimulus artefact suppressor for EMG recording during FES by a constant-current stimulator," Medical & Biological Engineering & Computing, vol. 31, No. 1, 1993, pp. 72-75.
Nam, Y., et al., "A retrofitted neural recording system with a novel stimulation IC to monitor early neural responses from a stimulating electrode," Journal of Neuroscience Methods, vol. 178, No. 1, 2009, pp. 99-102.
Norman, J.J., et al., "Hollow microneedles for intradermal injection fabricated by sacrificial micromolding and selective electrodeposition," Biomed Microdevices, vol. 15, Apr. 2013, pp. 203-210.

(56) References Cited

OTHER PUBLICATIONS

O'Keeffe, D.T., et al., "Stimulus artifact removal using a software-based two-stage peak detection algorithm," Journal of Neuroscience Methods, vol. 109, No. 2, 2001, pp. 137-145.

Ortiz-Catalan, M., et al., "On the viability of implantable electrodes for natural control of artificial limbs: Review and discussion," BioMedical Engineering OnLine, vol. 11, No. 33, 2012, 24 pages.

Park, E.S., et al., "Measurement of Median Sensory Nerve Conduction Velocity in Koreans, using Somatosensory Evoked Potential," Yonsei Medical Journal, vol. 27, No. 3, 1986, pp. 227-233.

Park, J.I., "Preoperative Percutaneous Cranial Nerve Mapping in Head and Neck Surgery," Arch Facial Plast Surg., vol. 5, 2003, pp. 86-91.

Park, J-H., et al., "Tapered Conical Polymer Microneedles Fabricated using an Integrated Lens Technique for Transdermal Drug Delivery," IEEE Transactions on Biomedical Engineering, vol. 54, No. 5, 2007, pp. 903-913.

Peckham, P.H., et al., "Functional Electrical Stimulation for Neuromuscular Applications," Annual Review of Biomedical Engineering, vol. 7, 2005, pp. 327-360.

Polk, B.J., et al., "Ag/AgCl microelectrodes with improved stability for microfluidics," Sensors and Actuators B, vol. 114, 2006, pp. 239-247.

Prausnitz, M.R., "Microneedles for transdermal drug delivery," Advanced Drug Delivery Reviews, vol. 56, 2004, pp. 581-587.

Scott, R.N., et al., "Stimulus artefact in somatosensory evoked potential measurement," Medical and Biological Engineering and Computing, vol. 35, No. 3, 1997, pp. 211-215.

Searle, A., et al., "A direct comparison of wet, dry and insulating bioelectric recording electrodes," Physiological Measurement, vol. 21, No. 2, 2000, pp. 271-283.

Seror, P. "Comparative Diagnostic Sensitivities of Orthodromic or Antidromic Sensory Inching Test in Mild Carpal Tunnel Syndrome," Archives of Physical Medicine Rehabilitation, vol. 81, No. 4, 2000, pp. 442-446.

Tai, C., et al., "Bladder Inhibition by Intermittent Pudendal Nerve Stimulation in Cat Using Transdermal Amplitude Modulated Signal (TAMS)," Neurourology and Urodynamics, vol. 31, 2012, pp. 1181-1184.

Tanner, J.A., "Reversible Blocking of Nerve Conduction by Alternating Current Excitation." Nature, vol. 195, 1962, pp. 712-713.

Thorsen, R., "An Artefact Suppressing Fast-Recovery Myoelectric Amplifier," IEEE Transactions on Biomedical Engineering, vol. 46, No. 6, 1999, pp. 764-766.

Wagenaar, D.A., et al., "Real-time multi-channel stimulus artifact suppression by local curve fitting," Journal of Neuroscience Methods, vol. 120, No. 2, 2002, pp. 113-120.

Wermeling, D.P., et al., "Microneedles permit transdermal delivery of a skin-impermeant medication to humans," Proc. of the National Academy of Sciences, vol. 105, No. 6, 2008, pp. 2058-2063.

Wichmann, T., "A digital averaging method for removal of stimulus artifacts in neurophysiologic experiments," Journal of Neuroscience Methods, vol. 98, No. 1, 2000, pp. 57-62.

Zhao, H., et al., "Electrochemical polishing of 316L stainless steel slotted tube coronary stents," Journal of Materials Science: Materials in Medicine, vol. 13, 2002, pp. 911-916.

Zwarts, M.J., et al., "Multichannel Surface EMG: Basic Aspects and Clinical Utility," Muscle Nerve, vol. 28, No. 1, 2003, pp. 1-17.

Marshall DM, et al., "Sutureless nerve repair at the fascicular level using a nerve coupler", J Rehabil Res Dev 1989;26:63-76.

Extended European Search Report issued in corresponding European Application No. EP17849487.8, mailed Mar. 13, 2020.

Communication pursuant to Article 93(3) EPC mailed Nov. 25, 2022 in corresponding European Application No. EP17849487.8, 5 pages.

\* cited by examiner

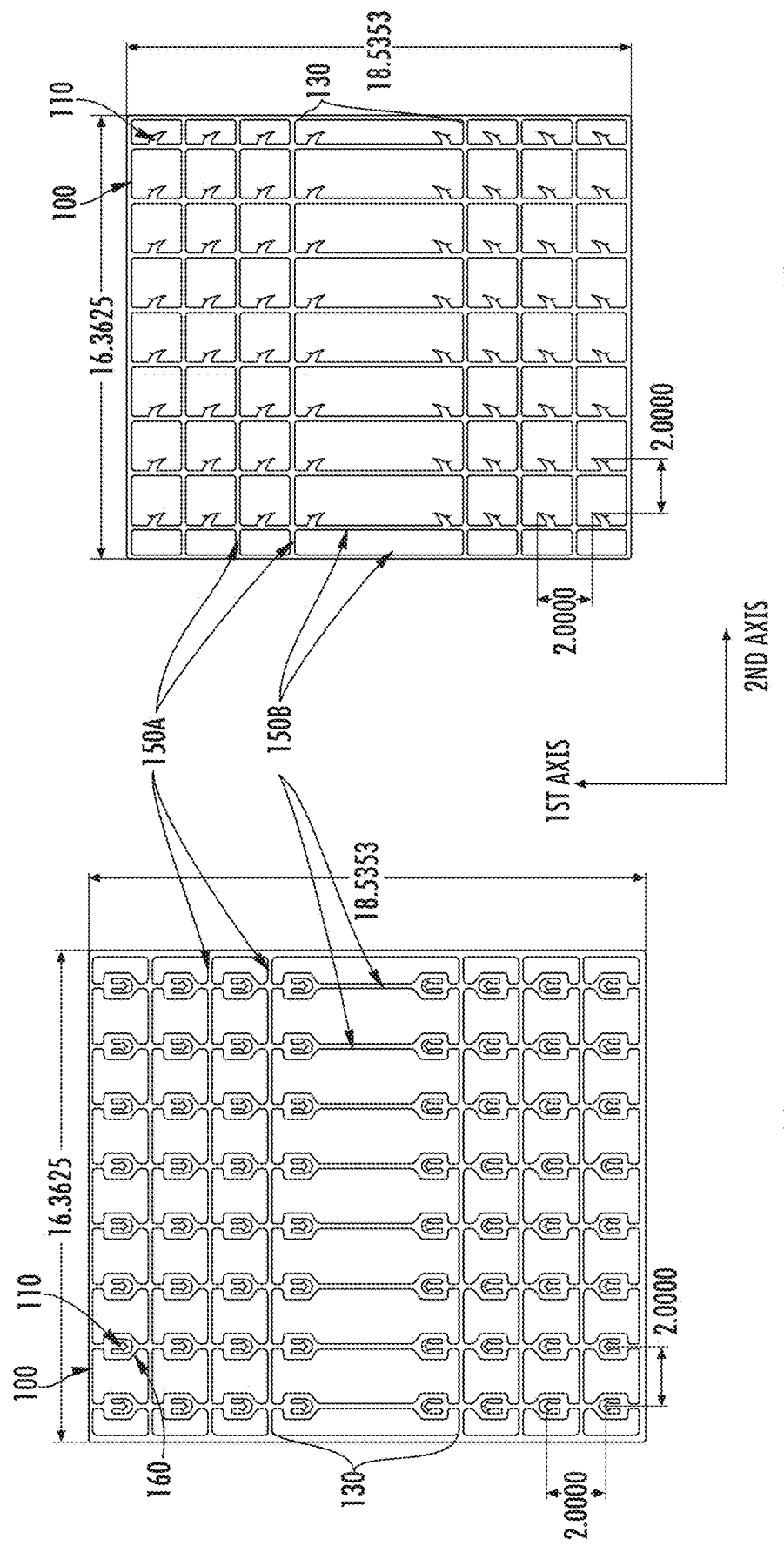

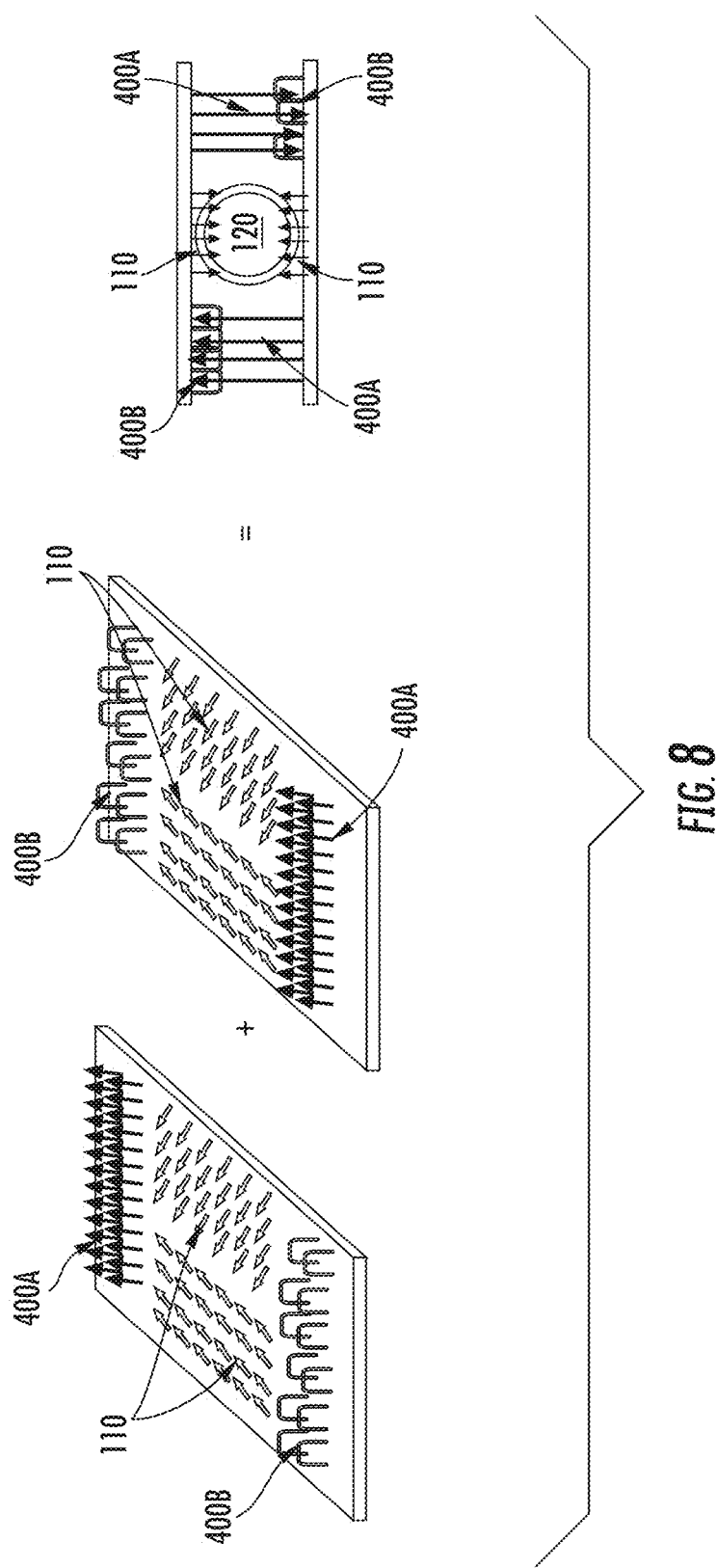

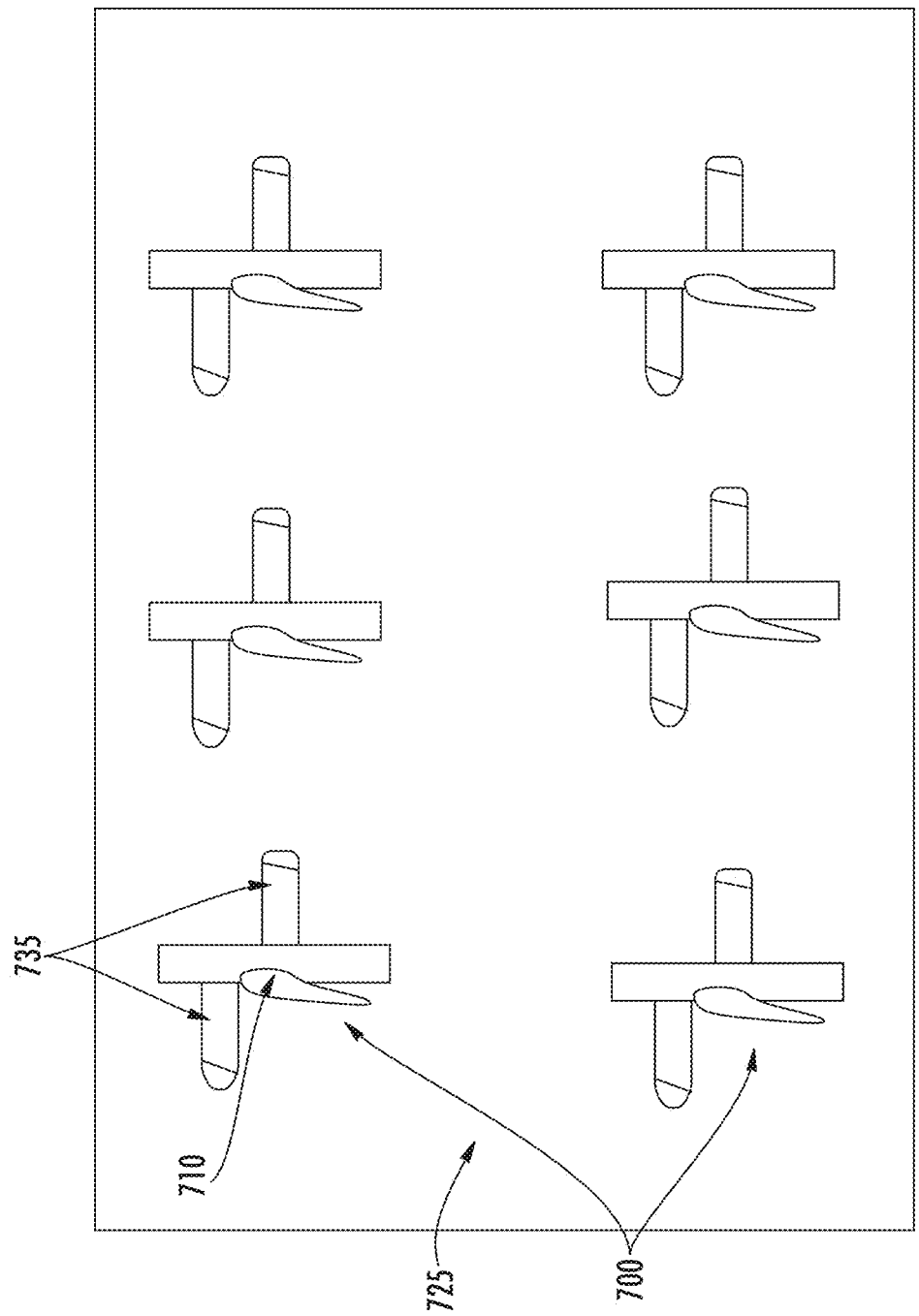

DEVICES AND METHODS FOR REPAIRING DAMAGE TO A TISSUE

CROSS-REFERENCE TO RELATED APPLICATIONS

This application is a continuation of U.S. patent application Ser. No. 17/519,817, filed on Nov. 5, 2021, which is a continuation of U.S. patent application Ser. No. 17/306,049, filed on May 3, 2021 (now U.S. Pat. No. 11,167,131), which is a continuation of U.S. patent application Ser. No. 15/697,358, filed on Sep. 6, 2017 (now U.S. Pat. No. 10,994,130), which claims the benefit of U.S. Provisional Patent Application No. 62/383,934, filed on Sep. 6, 2016, entitled "DEVICES AND METHODS FOR REPAIRING DAMAGE TO A NERVE," the disclosures of which are expressly incorporated herein by reference in their entireties.

BACKGROUND

Over a quarter of a million nerve injuries are reported annually in the United States alone. The majority of these injuries require surgical treatment, yet fewer than half recover to satisfactory levels. Nerve injuries affect up to 5% of all trauma cases, causing debilitating sensory deficits, paralysis, and muscular atrophy. Though the majority of these cases require surgical treatment, satisfactory recovery is only achieved about half of the time. The persistently poor prognosis following nerve repair is a complex problem involving poor axonal regeneration, secondary degeneration (e.g. muscle atrophy), and the technical aspects of surgical nerve repair. While much research has focused on improving axonal regeneration, the technical nuances of nerve coaptation have received less attention. Poor regenerative outcomes stem in large part from physiological limitations, but evidence suggests there are opportunities for improving nerve repair techniques.

From the perspective of battlefield medicine, advancements in body armor have improved soldier survival rates while exposing the extremities to levels of violence that would have previously been considered fatal. Amputation rates have increased, but enhancements in medical care and treatment delivery have allowed the salvage of even the most complex injuries. Return of satisfactory function even when a limb is "saved", however, remains a multifaceted challenge, as reconstruction and adequate healing of bones, soft tissues, muscles, blood vessels, and peripheral nerves must all be successful. Nerve repair in particular is a technically challenging exercise that requires advanced and specialized training. Even in experienced hands, nerve repair is time consuming and, as such, utilizes a disproportionate amount of resources. Several conventional nerve repair approaches are described below.

Microsutures: Microsuturing is the standard clinical practice for coapting the ends of a transected nerve. This method is technically challenging, requiring specialized microsurgical training, expensive equipment (e.g. operating microscope), and lengthy operative times. Despite the time and resources required, microsuture repairs are often inconsistent, with flaws in both the fascicular alignment and the spacing between nerve ends. Scar tissue associated with suture placement can impede axonal regeneration and be detrimental to nerve recovery. Although there is general disagreement regarding the size, number, and placement of microsutures, most surgeons agree that using the fewest number of sutures necessary and placing them as atraumatically as possible is the best approach.

A recent cadaver study showed that 40% of sutured nerve repairs examined were rated fair or poor in technical quality. A subsequent study agreed with these findings and suggested significant differences between "expert" and less proficient nerve surgeons in the ability to consistently obtain acceptable nerve alignment utilizing microsuture techniques. Perhaps related to these challenges, a 2014 survey revealed that 90% of hand surgeons currently use or would consider alternative nerve repair tools. A meta-analysis of median and ulnar nerve repairs indicated that less than 50% of all such repairs result in satisfactory functional recovery. Another study reported only 15 to 50 percent satisfactory results (depending on the level of injury) to ulnar nerves suffering military (blast and shrapnel) type injuries. Though suboptimal nerve recovery is a multifactorial, complex problem, any technical advances to improve potential axon regeneration would be beneficial.

Modern principles of neurorrhaphy include preparation of severed nerve ends by trimming back to healthy and viable tissue, proper alignment of approximated neural structures, and maintenance of this coaptation. Sutures are currently the gold standard for securing the repair but there is disagreement regarding size, number, and placement of these sutures. Indeed, while no specific suturing technique has proven superior, it is generally agreed upon that the fewest number of sutures necessary to hold the ends together should be used and these should be placed as atraumatically as possible. Scar tissue associated with suture placement is felt to impede axonal regeneration and may be detrimental to nerve recovery. Furthermore, nerve suturing is a technically demanding exercise requiring extensive specialized training and disproportionate operating room resources including expensive micro instruments, operating microscope, and time.

Fibrin glue and other tissue adhesives: Due to microsuturing limitations, alternate techniques, such as the use of tissue adhesives, in maintaining nerve coaptation have been introduced with varying degrees of success. The most rudimentary tissue adhesive consisted of a blood clot applied around approximated nerve ends. As would be expected, this method was plagued by inconsistency and unreliability. These issues were partly overcome with the introduction of commercially available "fibrin glue." Current preparations consist of two separate components that, when mixed together, create a fibrin clot. This clot can be applied around approximated nerve ends and shaped into a cylinder using a pliable background such as rubber sheeting. As the "glue" sets up, the fibrin clot interdigitates into and adheres to the surface of the nerve and mechanically couples the nerve ends together. This technique is faster and easier than formal suturing and can be adequately performed by someone even without significant microsurgical skills.

This method, however, has two main limitations. The first is that the surgeon is "blinded" to fascicular alignment during the application process. Though alignment can be grossly obtained prior to "gluing," verification and maintenance of this alignment is difficult while the cylinder of fibrin clot is setting up. The second limitation is related to the glue's holding strength, which many argue is inadequate. Indeed, biomechanical testing of fibrin glue (used to augment a simple suture repair) did not demonstrate any additional holding strength over sutures alone.

So far, attempts to overcome these shortcomings have not been successful. Cyanoacrylate based adhesives (similar to commercially available SUPER GLUE from the Super Glue Corp. of Ontario, Canada) have had limited success in animal studies. With some studies suggesting neurotoxicity, extensive inflammatory reactions, and the production of toxic break down products including formaldehyde, a significant role in clinical nerve repair seems unlikely. Furthermore, inadvertent placement of this adhesive between approximated nerve ends would clearly block regenerating axons. Albumin, soldered across the coaptation site using a laser, can act as "spot welds" to hold the nerve ends together. The technique may cause thermal damage to the nerve tissue, and, at the very least, is expensive (i.e. the laser) and cumbersome.

Several reports published in the late 1960's noted that SteriStrips (e.g., NEXCARE STERI-STRIPS from 3M Corp. of Maplewood, MN) (a non-woven fabric of viscose rayon, with an adhesive co-polymer of iso-octylacrylate and acrylic acid strips typically used to hold skin edges together) could effectively be used to repair rodent sciatic nerves and canine inferior alveolar nerves. Early inflammation was noted to be extensive but at late follow up was minimal and confined to the outside of the tape. Despite some promising, albeit anecdotal, clinical results (especially in very small facial nerves), there is no mention of this technique after the 1960's. Based on the understanding of this particular product, and supported by isolated reports of product extrusion, the negative effects of foreign body reaction and chemical irritation may have been more significant than early reports indicated.

Nerve conduits and entubulation: The use of nerve conduits (i.e., cuffs) as nerve couplers (for primary repair, not to overcome a gap) has several advantages. Approximated nerve ends are placed in either end of a nerve conduit with the cut surfaces barely touching or just a few millimeters apart. Sutures placed through the edges of the conduit and the corresponding epineurium maintain the coaptation. This technique is technically easier than formally suturing the nerves together and moves the trauma (and scarring) associated with suture placement away from the regenerating axons at the end of the nerve stump. Displacing sutures from the injury site also disseminates tension away from the nerve ends, which has been shown to improve axon regeneration in animal models. The conduit creates a protected microenvironment between the nerve ends allowing for a concentration of neurogenic and trophic factors, blocks invading scar tissue, and blocks escaping axons (which may decrease neuropathic pain at the repair site). The space between nerve ends allows for nerve swelling and may, though this is controversial, potentiate neurotropic mechanisms. Evans et al., Selective reinnervation: A comparison of recovery following micro suture and conduit nerve repair, Brain Res., 1991; 559(2):315-321 demonstrated that while correct alignment of approximated nerve ends was best, purposefully misaligned rodent sciatic nerves recovered better if coupled with a nerve conduit verses direct suture repair. Lundborg et al., Tubular repair of the median or ulnar nerve in the human forearm: a 5-year follow-up, Journal of hand surgery, 2004; 29(2):100-7, in a prospective human trial, demonstrated regeneration across 5 mm gaps in large major peripheral nerves repaired with nerve conduits to be clinically equivalent to direct repair. Disadvantages with this technique include the need for microsurgical skills, difficulty aligning nerve ends, and concerns with size mismatches. In other words, gapping at the nerve/lumen interface may negate the protected microenvironment and may allow scar accumulation between nerve ends. Entubulation strategies additionally reduce the tendency for over-approximation of fascicles common in microsuture-only repair. In fact, less-proficient surgeons were able to coapt nerve ends at or near "expert" levels when using conduits to augment their suture repairs. Despite the benefits of entubulation, conduit-assisted repairs still require microsuturing and its associated drawbacks.

In summary, owing to the limitations of microsuture repair, multiple alternatives have been developed. Commercial fibrin glues suffer from inadequate adhesive strength, obscured visualization during fascicular alignment, and are not Food and Drug Administration (FDA) approved for this application. Other tissue adhesives, such as cyanoacrylates, have had limited success in animal studies, but inflammatory reactions, toxicity, and the potential for adhesive impeding regeneration prevents widespread adoption. As another example, Albumin can be "spot welded" across the coaptation site, but this requires an expensive laser that can thermally damage nerve tissue. Conduit-assisted nerve repairs have several advantages, but these still require use of microsutures.

SUMMARY

An example device for repairing a nerve is described herein. In some implementations, the example device combines the advantages of repair-site entubulation with a means for mechanical attachment superior to microsutures.

An example device for repairing a nerve can include a flexible carrier layer made of a biologic material, and a metallic support member including a plurality of micro-protrusions extending therefrom. The metallic support member can be at least partially integrated with the flexible carrier layer. Additionally, the flexible carrier layer can be configured to cover at least a portion of the nerve, and the micro-protrusions can be configured to attach to a superficial tissue of the nerve.

Alternatively or additionally, the micro-protrusions can be sized and shaped to pierce the outer epineurium of the nerve. Optionally, the micro-protrusions can be sized and shaped to not pierce a fascicle of the nerve.

Alternatively or additionally, the metallic support member can be a superelastic alloy. For example, the superelastic alloy can be of a composition that comprises nickel and titanium.

Alternatively or additionally, the biologic material can be small intestine submucosa (SIS).

Alternatively or additionally, the flexible carrier layer can be a two-dimensional sheet. For example, the flexible carrier layer and metallic support structure can be nerve tape when integrated together. Optionally, the flexible carrier layer can be configured to entubulate a repair site. Alternatively, the flexible carrier layer can optionally be configured to sandwich a repair site. In some implementations, the flexible carrier layer can include a wrapping portion for maintaining entubulation or sandwiching of the repair site. In other implementations, the device can include a fastener for maintaining entubulation or sandwiching of the repair site.

Alternatively or additionally, the micro-protrusions can be bent out of plane with respect to the metallic support member in a direction of a first axis or a second axis of the metallic support member. For example, in some implementations, the micro-protrusions can be bent out of plane with respect to the metallic support member in the direction of the first axis, where the first axis substantially corresponds to an axis along a length of the nerve. In other implementations, the micro-protrusions can be bent out of plane with respect to the metallic support member in the direction of the second axis, where the second axis substantially corresponds to an axis following a circumference of the nerve Alternatively or additionally, the micro-protrusions can include a first group of micro-protrusions and a second group of micro-protrusions, where the first and second groups of micro-protrusions are oriented in opposite directions. Optionally, the first and second groups of micro-protrusions can be oriented to face each other. Alternatively or additionally, the micro-protrusions are not arranged in a region of the surface of the metallic support member in proximity to a repair site. Alternatively or additionally, the first and second groups of micro-protrusions can be arranged in different regions on a surface of the metallic support member.

Alternatively or additionally, the metallic support member can be a planar base, and the micro-protrusions extend from a surface of the planar base.

Alternatively or additionally, the micro-protrusions can form an array of interconnected micro-protrusions. For example, in some implementations, the metallic support member can include a plurality of intersecting cross bridges, and the micro-protrusions can be interconnected via the intersecting cross bridges. Optionally, at least one of widths of the intersecting cross bridges or spaces between the intersecting cross bridges can be configured to optimize at least one of strength or flexibility of the metallic support member. Alternatively or additionally, in some implementations, cross bridges extending in a direction substantially corresponding to an axis following a circumference of the nerve are not provided in proximity to a repair site.

Alternatively or additionally, the metallic support member can optionally include at least one extending feature configured to at least partially surround a micro-protrusion.

Alternatively or additionally, the metallic support member can include a plurality of elongate strips, and the micro-protrusions can extend from the elongate strips. For example, the elongate strips can extend in a direction substantially corresponding to an axis along a length of the nerve.

Alternatively or additionally, each of the elongate strips can include one or more projecting members. Optionally, the elongate strips are not provided in proximity to a repair site. Alternatively or additionally, the elongate strips can be free floating within the flexible carrier layer.

Alternatively or additionally, at least one of the flexible carrier layer or the metallic support member can be configured for drug delivery or cell transplantation.

Alternatively or additionally, the micro-protrusions can be at least one of micro-hooks or micro-needles.

Alternatively or additionally, at least one of the micro-protrusions can be a barb.

Alternatively or additionally, at least one of the metallic support member or the micro-protrusions can be configured for delivering electrical stimulation or recording electrical activity.

Alternatively or additionally, the device can optionally include a plurality of flexible carrier layers, each flexible carrier layer being a biologic material. In addition, the metallic support member can be sandwiched between the flexible carrier layers.

An example method for repairing a nerve is also described herein. The method can include macroscopically positioning a device comprising a plurality of micro-protrusions extending therefrom in proximity to the nerve, and covering at least a portion of the nerve with the device. The micro-protrusions can be configured to attach to a superficial tissue of the nerve.

Alternatively or additionally, the micro-protrusions can attach to the superficial tissue of the nerve before the nerve is entubulated by the device.

Alternatively or additionally, the method can further include at least one of applying an electrical stimulus to the nerve via the micro-protrusions or recording electrical activity from the nerve via the micro-protrusions.

Alternatively or additionally, the device can be attached to the nerve without sutures Alternatively or additionally, at least one of positioning the metallic support member or covering the at least a portion of the nerve with the metallic support member can be performed using a tool.

Another example device for repairing a nerve is described herein. The device can include a support member including a plurality of micro-protrusions extending therefrom. The support member can be configured to cover at least a portion of the nerve, and the micro-protrusions can be configured to attach to a superficial tissue of the nerve.

Another example device for repairing a nerve is described herein. The device can include a flexible carrier layer made of a biologic material, and a metallic support member including a micro-protrusion extending therefrom. The metallic support member can be at least partially integrated with the flexible carrier layer. Additionally, the flexible carrier layer can be configured to cover at least a portion of the nerve, and the micro-protrusion can be configured to attach to a superficial tissue of the nerve. In some implementations, the device can include a plurality of metallic support members, each metallic support member comprising a micro-protrusion extending therefrom.

Yet another example device can include a planar (or curved) base including a plurality of micro-protrusions on a surface thereof. The planar base can be configured to cover at least a portion of the nerve, and the micro-protrusions can be configured to attach to a superficial tissue of the nerve.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 4A and 4B illustrate other example devices for repairing a nerve. In FIG. 4A, the micro-protrusions bend out of plane in a direction that substantially corresponds to an axis along a length of the nerve (i.e., along a longitudinal axis of the nerve). In FIG. 4B, the protrusions bend out of plane in a direction that substantially corresponds to an axis following a circumference of the nerve.

In FIG. 6, the nerve repair device is wrapped around the nerve 120.

In FIG. 7, a plurality of nerve repair devices (e.g., two devices) are used to sandwich the nerve 120.

FIG. 8 illustrates another example nerve repair device, wherein the micro-protrusions 110 can attach to the nerve 120 and hook and loop type fasteners 400A, 400B are used to close the device after wrapping, sandwiching, etc. In FIG. 8, a plurality of nerve repair devices (e.g., two devices) are used to sandwich the nerve 120.

In FIG. 9A, a micro-protrusion 210 (e.g., microhook) is shown with a microhook opening 225 formed in the metallic support structure. The micro-protrusion 210 deforms deeper into tissue during loading, which is shown by arrow 500.

FIG. 10A illustrates a metallic support member 600 made of nickel-titanium (NiTi) or Nitinol with a plurality of micro-protrusions 610 extending therefrom. The metallic support member 600 is integrated with a flexible carrier layer 625 made of SIS. FIG. 10B illustrates the nerve repair device applied on a nerve 120. All of the horizontal crossbars of the Nitinol mesh shown in FIG. 10B are disconnected. This design eliminated mesh resistance to wrapping and risk of crimping. The hybrid SIS/Nitinol construct shown in FIG. 10B exhibited excellent handling properties and was fully conformable to the nerves during wrapping. This close contouring of the nerves resulted in a secondary benefit. Microhooks more fully engaged the outer nerve tissues, and device attachment strength increased 40%, even as microhooks had been shortened by over 15%.

FIGS. 11A and 11B illustrate a metallic support member 600 made of nickel-titanium (NiTi) or Nitinol with a plurality of micro-protrusions 610 extending therefrom. The metallic support member 600 includes a plurality of elongate strips 650, each elongate strip having projecting members 635. The metallic support member 600 is integrated with a flexible carrier layer 625. FIG. 11C illustrates the nerve repair device applied on a nerve 120.

FIG. 15 illustrates another example device for repairing a nerve.

DETAILED DESCRIPTION

Figure 1:
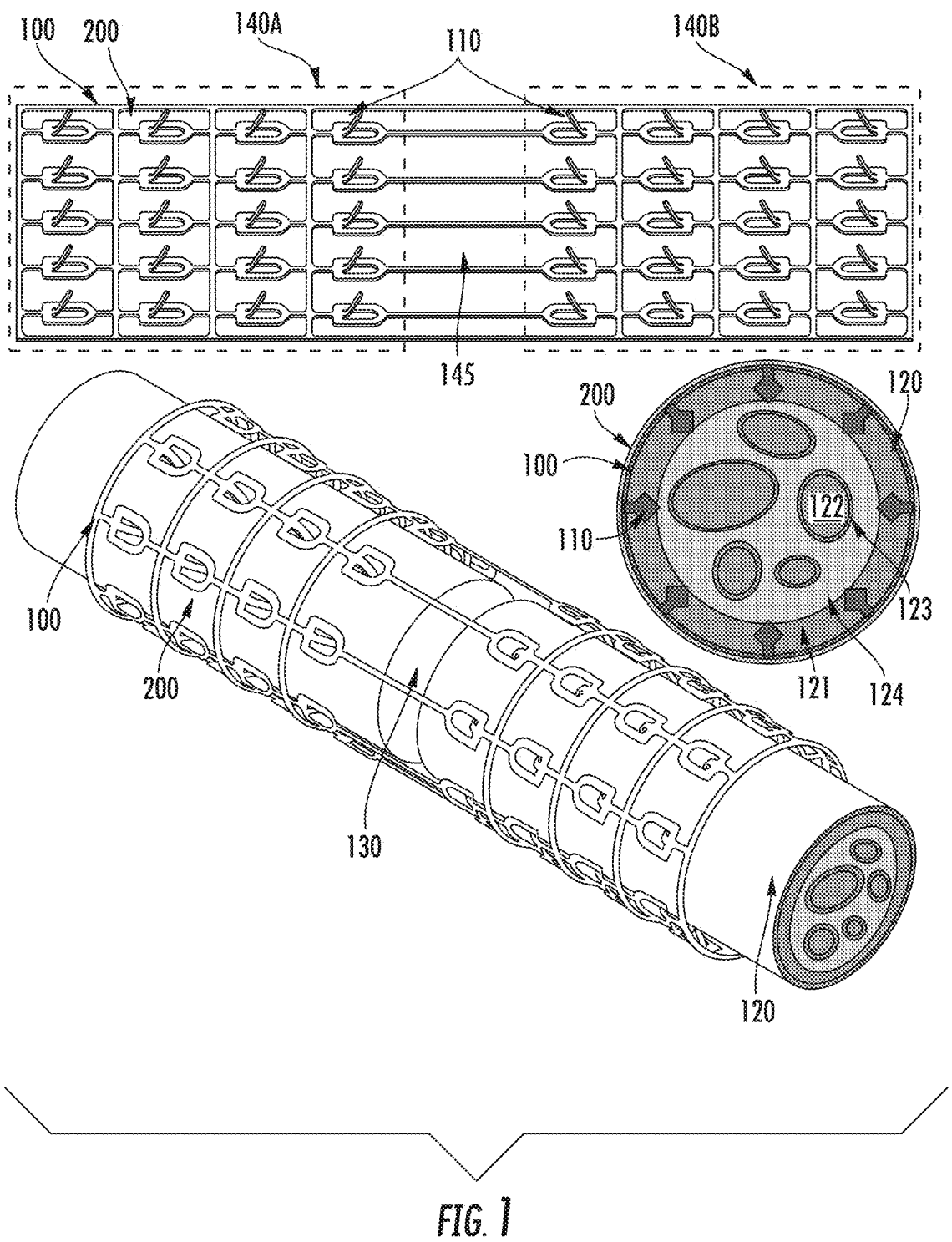
FIG. 1 illustrates an example device for repairing a nerve.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for repairing a transected nerve, it will become evident to those skilled in the art that the implementations are not limited thereto, but are applicable for repairing other damage to a nerve and/or repairing other tissue. For example, other tissues may include muscle, tendons, vasculature, or skin, fascia, or solid organs (like the liver). The devices and methods described herein may also be used in hernia repairs or to patch defects in tissues, such as tendon defects in rotator cuff repairs. The devices and methods described herein may also be specialized for repair tissues of two different types, such as tendon-to-bone repairs as in rotator cuff surgeries.

Example Nerve Repair Device

A nerve repair device can be easy to apply, efficient, atraumatic, and improve both the mechanical alignment and the neurotrophic environment. One way to conceptualize such a tool is by combining the advantages of nerve repair entubulation with a means of effective mechanical attachment, superior to microsutures.

Microfabrication technology can be used to create individual, or arrays of, micro-protrusions (e.g., microneedles or microhooks) incorporated into a nerve coupling device that optionally entubulates the nerve repair site. In some cases, collaborating clinicians evaluating prototype microhook arrays described herein were motivated by the mechanical properties of the devices. Specifically, the barbed microhooks were found to be remarkably effective at mechanically fastening to the outer connective tissue layers of nerves, without penetrating to the depth of interior fascicles.

Referring now to FIG. 1, an example device for repairing a nerve 120 is shown. The nerve 120 shown in FIG. 1 is a transected nerve, and the repair described is coaptation. It should be understood that the device described herein can be used for repairing other types of nerve damage. For example, the device described herein can be used for nerve gap repairs (e.g., where a conduit is provided between ends of a transected nerve), allograft, autograft, and/or xenograft. Additionally, it should be understood that the device described herein can be used to repair other types of tissues including, but not limited to, muscle, tendon, solid organs (e.g., liver, kidneys, etc.), bladder, uterus, fascia, hernia repair, vasculature, or skin. Thus, this disclosure is not intended to be limited to repairing a transected nerve with the device, which is provided only as an example.

The device can include a support member having a plurality of micro-protrusions 110 on a surface thereof. As described herein, the support member can be a planar base (e.g., a substantially two-dimensional sheet as shown in FIG. 1) or a plurality of elongate strips (e.g., as shown in FIGS. 4A-4B, 10A-10B, and/or 11A-11C). The support member can optionally be a metallic support member. In some implementations, the metallic support member is stainless steel. In other implementations, the metallic support member is a superelastic (or pseudoelastic) alloy. Superelasticity is a type of mechanical shape memory. For example, superelastic alloys can be deformed by strains as high as 10% and still return their original state. Nitinol is an example superelastic alloy of nickel and titanium widely used in medical devices based on its biocompatibility and unique mechanical properties. Whereas traditional metals like stainless steel deform elastically only to about 1%, Nitinol behaves "super elastically," exhibiting properties similar to biological materials such as tendon or bone and returning to its formed shape even after strains of up to 10%. Thus, Nitinol can be even be "crumpled" and still return to its original shape, making it highly resistance to kinking and crimping. The use of Nitinol also increases conformability of the device. It should be understood that this disclosure contemplates that the support member can be formed from other materials including, but not limited to, other superelastic alloys such as gold cadmium (AuCd), copper zinc aluminum (CuZnAl), or copper aluminum (CuAl). Optionally, the support member can be integrated with a flexible carrier layer 200. As described herein, the flexible carrier layer 200 can be formed from biocompatible, biodegradable, or bioresorbable material. In some implementations, the flexible carrier layer 200 can be formed from a biologic material or processed biologic material. A processed biologic material is derived from a living being (e.g., human, cow, pig, etc.) and processed to remove the cells and leave just the extracellular matrix (ECM), etc. behind. Example processed biologic materials include, but are not limited to, small intestine submucosa (SIS), collagen, amniotic, or other tissue. In some implementations, the support member can be attached to or bonded to a surface of the flexible carrier layer 200. Alternatively, the support member can be at least partially embedded within the flexible carrier layer 200. Optionally, in some implementations, the device includes a plurality of flexible carrier layers, and the support member is sandwiched (e.g., laminated) between a plurality of flexible carrier layers. The integrated support member and flexible carrier layer 200 can form a nerve tape as described herein.

As shown in FIG. 1, the device can include a support member 100 (referred to in FIG. 1 as "planar base 100") including a plurality of micro-protrusions 110 on a surface thereof. As used herein, a planar base is a substantially two-dimensional base, e.g., a relatively thin sheet of material. Optionally, the planar base can be flexible. In some implementations, the planar base can optionally be flat. Alternatively, in other implementations, the planar base or portions thereof can optionally be bent or curved. This disclosure contemplates that the planar base can have any shape and/or size for repairing the damaged nerve. The planar base can be configured to cover at least a portion of the nerve 120, and the micro-protrusions 110 can be configured to attach to a superficial tissue of the nerve 120. The planar base can be flexible enough to wrap around at least a portion of the nerve 120. In other words, the planar base can be flexible enough to be positioned on the nerve 120 and bent or wrapped to follow the contoured surface of the nerve 120. For example, the micro-protrusions 110 can be configured to attach to the epineurium (outer epineurium) without penetrating into the interior portions of the nerve where the axons reside (internal fascicles), which minimizes atraumatic penetration. For example, the micro-protrusions 110 can be configured to attach to the outer epineurium 121 but without piercing a fascicle 122 (i.e., bundle of axons). Optionally, the micro-protrusions 110 can be configured to attach to the outer epineurium 121 but without piercing the perineurium 123. The outer epineurium 121, fascicle 122, perineurium 123, and inner epineurium 124 of the nerve 120 are labeled in FIG. 1 for reference. Alternatively or additionally, in some implementations, the micro-protrusions 110 can be sized and shaped to penetrate the nerve 120 to a depth between about 100 µm and about 1 mm, and optionally to penetrate the nerve 120 to a depth between about 200 µm and about 500 µm.

Figure 7:
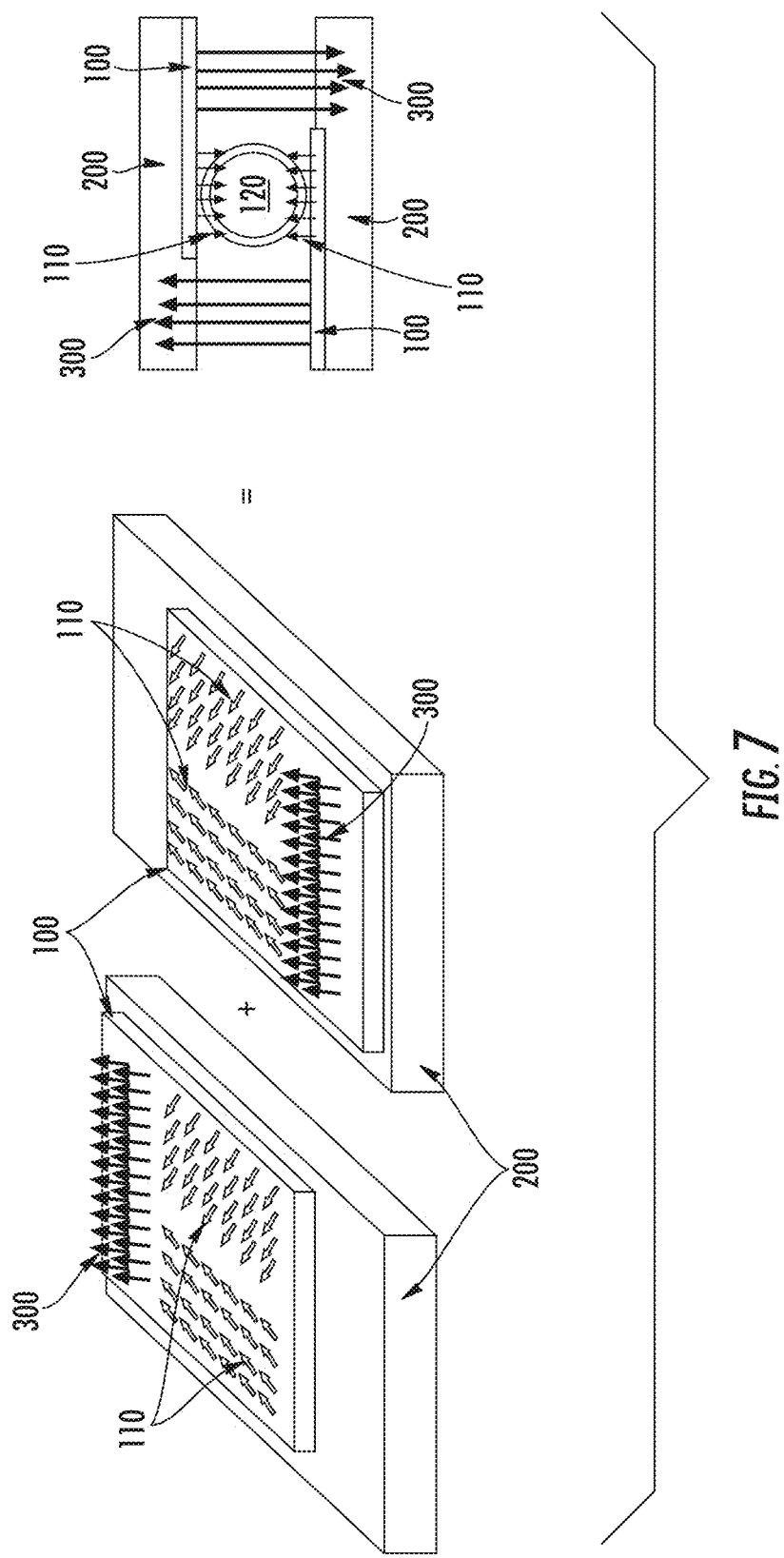
FIG. 7 illustrates another example nerve repair device, wherein the micro-protrusions 110 can attach to the nerve 120 and longer fastening hooks 300 separately attach to the flexible substrate 200 itself after wrapping, sandwiching, etc.
Figure 9A:
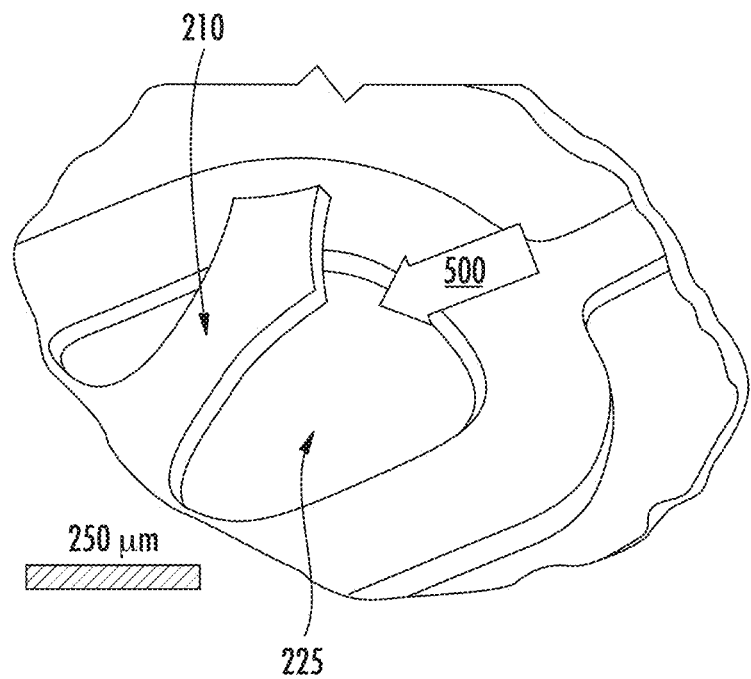
FIG. 9A illustrates a "trapdoor" design for a micro-protrusion (e.g., microhook).
Figure 9B:
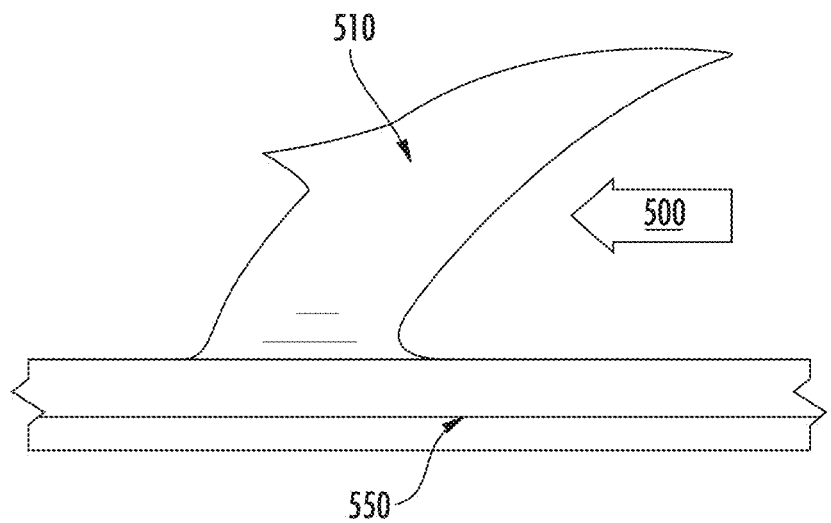
FIG. 9B illustrates a modified design for a micro-protrusion 510. The micro-protrusion 510 is bent out of plane in a direction substantially corresponding to an axis along a length of a nerve. The micro-protrusion 510 has increased resistance to deformation during loading, which is shown by arrow 500, as compared to the micro-protrusion shown in FIG. 9A.
Figure 10A:
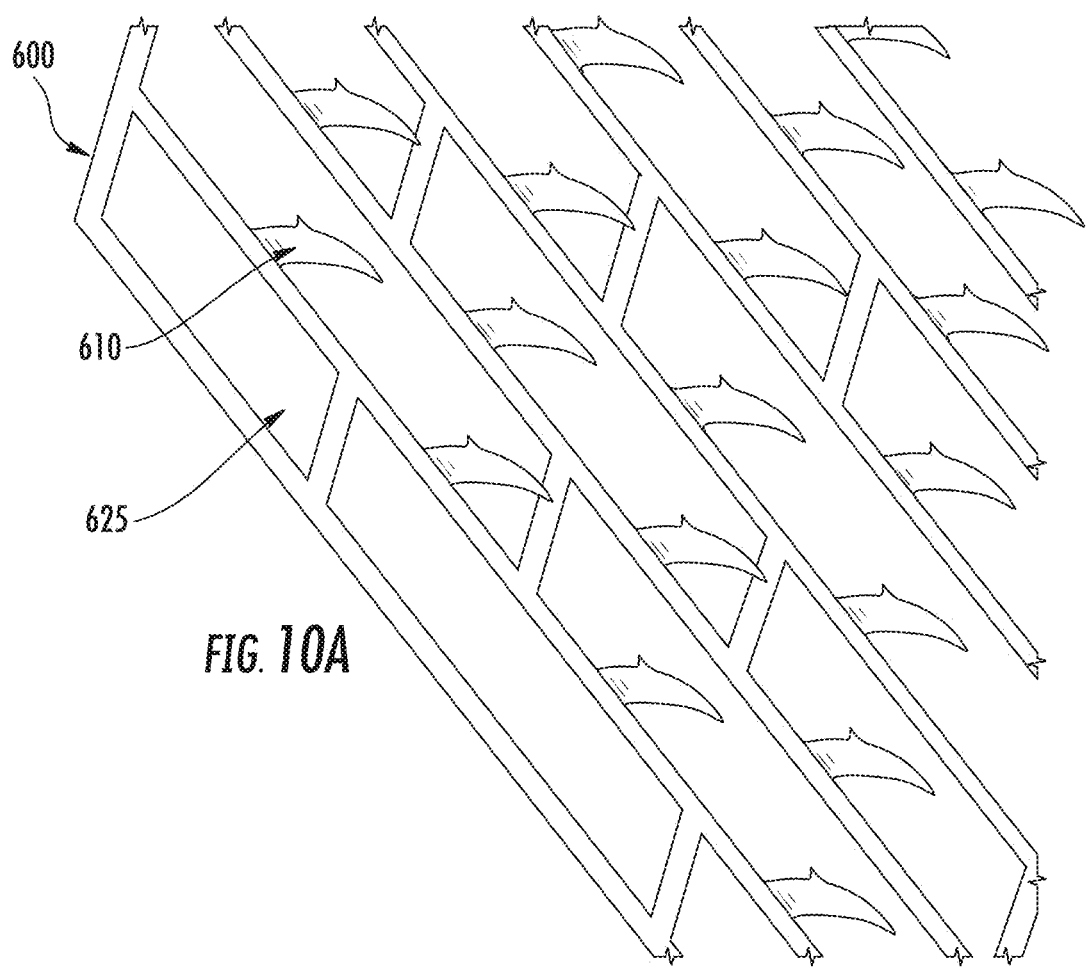
FIGS. 10A and 10B illustrate another example nerve repair device.
Figure 10B:
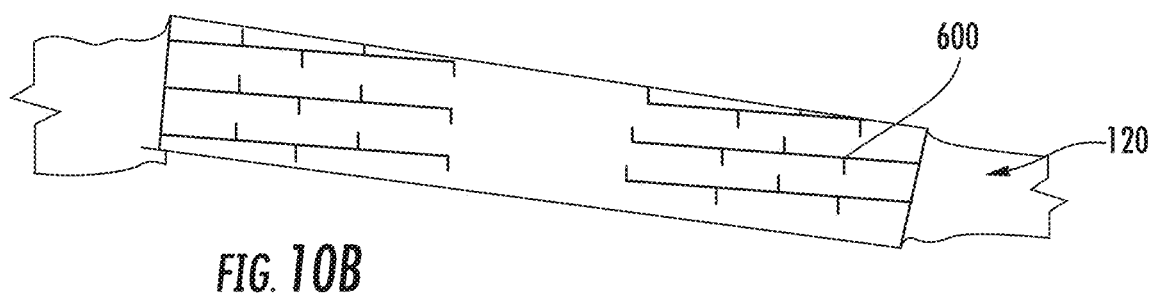

In some implementations, the planar base (and/or optionally the flexible carrier layer if provided) can be configured to entubulate a repair site 130. For example, in FIG. 1, the repair site 130 is a coaptation site, and the planar base 100 entubulates the repair site 130. As noted above, it should be understood that a coaptation site is provided only as an example and that this disclosure contemplates using the device to repair other nerve damage. Optionally, the planar base can include at least one tapered edge. For example, the planar base can define a substantially triangular or trapezoidal shape. As described herein, when the planar base has at least one tapered edge (e.g., the planar base is triangular), the planar device is designed to fasten to itself. In other implementations, the planar base 100 (and/or optionally the flexible carrier layer if provided) can be configured to sandwich the repair site 130 (e.g., as shown by the devices of FIGS. 7 and 8).

The micro-protrusions 110 can include a first group 140A of micro-protrusions 110 and a second group 140B of micro-protrusions 110, where the first group 140A and second group 140B of micro-protrusions 110 can be oriented in opposite directions. For example, the first group 140A and second group 140B of micro-protrusions 110 can optionally be oriented to face each other. Alternatively or additionally, the first group 140A and second group 140B of micro-protrusions 110 can be arranged in different regions on the surface of the planar base 100 as shown in FIG. 1. Optionally, the micro-protrusions 110 are not arranged in a region 145 of the surface of the planar base 100 in proximity to the repair site 130. This creates a "demilitarized zone," which can shift tension away from the nerve ends at the repair site 130, which avoids trauma where the axons regenerate.

A number of example prototypes, which include of a thin substrate based mesh of barbed micro-protrusions (e.g., microneedles) embedded in a flexible backing substrate (also sometimes referred to herein as "flexible carrier substrate"), are described herein. These constructs can be macroscopically positioned and wrapped around coapted nerve ends to bind and entubulate the repair site. This construction confers the advantages of conduit repair without the need for microsutures. Preliminary experiments demonstrated easy application and acceptable mechanical attachment of nerve ends.

Devices such as those shown in FIG. 1 can be developed into an FDA-approved "microhook nerve tape" that can be stored on the shelf for use in surgical repair of injured or transected nerves. The nerve tape product could be quickly and effectively applied to reliably coapt nerves with technical accuracy normally requiring a microscope and specialized surgeon. Although "microhook nerve tape" is used herein as an example, it should be understood that this disclosure contemplates a nerve tape with micro-protrusions (e.g., micro-needles or other micro-protrusions). Entubulation of the repair site, redistribution of forces, and biocompatible materials will further improve outcomes. For these reasons microhook nerve tape has the potential to drastically reduce nerve repair costs while improving patient access and quality of recovery.

A workable microhook nerve tape, as the name implies, can quickly and efficiently coapt severed nerve ends. By eliminating the need for meticulous micro suture placement, surgeons less proficient in microsurgical techniques but knowledgeable in the principles of nerve repair could perform effective repair surgeries. Additionally, without the need for microsuturing, nerve repairs could be done in "tighter" spaces, decreasing the necessary exposure as well as the associated extra dissecting and scarring. Even defects requiring grafting would benefit as the microhook nerve tape could be used at either end of the graft and to effectively combine and stack nerve graft strands when multi-strand or cable grafting techniques were necessary for larger diameter nerve repairs. Unlike other attempts to circumvent the need for sutures, microhook nerve tape would require no specialized equipment (e.g., lasers) or need for refrigeration. This improves access and expedites treatment of, for example, soldiers suffering from nerve injuries and should result in better utilization of surgical and medical resources.

For example, in some implementations, microhook nerve tape can be applied as follows: 1) place the nerve tape at the floor of the nerve repair site, 2) lift and place the nerve stumps on each side of the nerve tape to face each other, 3) wrap the nerve tape around the partially secured nerve ends so that the remaining microhooks engage the outer epineurium, and 4) completely wrap the self-sealing microhook nerve tape to entubulate the coaptation site. Accordingly, nerve tape can be positioned quickly and macroscopically, and is unaffected by slight inaccuracies in nerve placement. Well-performed clinical studies of conduit repairs have demonstrated that small gaps between entubulated nerve ends does not adversely affect recovery. Additionally, slight misalignments between coapted nerve ends are self-corrected during wrapping. In addition to providing the regenerative benefits of entubulation, the arrayed microhooks spread tension across a broader area of the outer epineurium. Distributing tension in nerve repairs has been shown to improve axon regeneration in animal models.

Microhook nerve tape combines the advantages of entubulation with microfabrication technology to create a device for nerve coaptation. An array, or mesh, of microhooks can provide the same or superior attachment strength of microsutures, while distributing coaption forces across a broader area of more superficial tissue, to avoid damage to interior fascicles.

In addition improved surgical efficiency and resource expansion (e.g., more surgeons capable of performing nerve repairs), there would be expected improvements in nerve repair outcomes, as well. The microhook nerve tape concept offers several such advances including isolation and protection of the repair site, alleviation of tension at the repair site, and avoidance of suture induced trauma and the subsequent axonal impeding scar tissue. Hook design will be aimed at maximizing holding forces while minimizing nerve tissue damage.

Nerve coaptation techniques have remained largely unchanged for several decades, relying on the use of microsutures to appose nerve ends. Microhook nerve tape can provide an alternative, reducing the technical challenges, operating room time and resources required for nerve repair, while offering improved outcomes. Additionally, microhook nerve tape can offer the ability to custom entubulate the nerve repair utilizing the same mechanical holding characteristics of microsutures. This will provide a powerful tool for peripheral neurosurgery. As such, more surgeons could perform nerve repair surgery, decreasing the need for referral to tertiary care centers (which may require a significant amount of travel). Since the surgery would be faster, these surgical procedures would require less operating room and surgical personnel time-both valuable resources. Repairs could potentially be done through smaller incisions, resulting in smaller and less morbid surgical scars.

Suturing severed nerves together is, by convention, the gold standard, but sutures traumatize nerve tissue resulting in scar tissue that impedes nerve fiber regeneration. Microhook nerve tape avoids this trauma at the nerve repair interface and can actually decrease intervening scar tissue by isolating and protecting the coaptation site. This isolation also allows the accumulation of neurotrophic growth factors and blocks escaping nerve fibers. The mechanical coupling built into the microhook nerve tape can securely maintain nerve alignment and can dissipate detrimental tension at the repair site. Optionally, a tissue adhesive (e.g., a tissue adhesive layer) can also be incorporated into the microhook nerve tape. These improvements could translate to improved nerve regeneration and improved functional recovery from nerve injuries.

Advantages of the microhook nerve tape described herein include improved surgical efficiency and resource expansion, and potentially improved outcomes due to a more a "biologically friendly" technique. Microhook nerve tape can effectively lower the technical skills required to perform a nerve repair, e.g., experienced nerve surgeons could perform coaptations faster and surgeons with less microsurgical skills could now treat injuries previously requiring transfer to a higher level of care. Surgery could even be done with potentially less dissection as repairs could be done in a "tighter space" requiring less exposure.

Biological advantages of the microhook nerve tape described herein include increased isolation of the nerve repair microenvironment, better dissemination of tension away from the repair site, and a shifting of "suture" trauma away from the nerve ends. For example, with reference to FIG. 1, the micro-protrusions 110 grab the outer epineurium of the nerve 120 proximal and distal to the repair site 130 (i.e., the coaptation site). In other words, the micro-protrusions can be sized and shaped to pierce the outer epineurium of the nerve. Additionally, the micro-protrusions can be sized and shaped to not pierce the internal region of the nerve so as to not damage the region where axons reside. For example, the micro-protrusions can be sized and shaped to pierce the outer epineurium but without piercing a fascicle (i.e., bundle of axons). Optionally, the micro-protrusions can be sized and shaped to pierce the outer epineurium without piercing the perineurium. Alternatively or additionally, in some implementations, the micro-protrusions can be sized and shaped to penetrate the nerve to a depth between about 100 µm and about 1 mm, and optionally to penetrate the nerve to a depth between about 200 µm and about 500 µm. Though some micro-trauma would be expected at the interface between the device and the nerve 120, the detrimental effects of suture generated scar tissue on axonal regeneration can be minimized. Optionally, there is a "demilitarized zone" in region 145 on the surface of the planar base 100 as shown in FIG. 1. By both grabbing the nerve away from the coaptation site, and optionally with tissue adhesive, tension can be alleviated and dispersed away from the nerve ends. The negative effects of focal tension on nerve regeneration are well established and include increased scarring, impaired axonal advancement, decreased perfusion, and diminished Schwann cell activation. These effects can be at least blunted by redistributing the tension.

Microhook nerve tape offers several advantages over conventional repair techniques, including but not limited to, the following:
1) Easy and efficient application: Preliminary experimentation revealed rapid and technically accurate alignment could be obtained without microsurgical technique or a surgical microscope.
2) Improved technical accuracy of repairs: Conduit-assisted repairs decrease the tendency for "over approximation" of nerve ends and improve fascicular alignment.
3) Enhanced biological environment: Entubulation of the repair prevents axons from escaping and scar tissue from invading the coaptation site. Neurotropic and growth factors are also contained.
4) Minimal damage to vital nerve elements: The microhooks penetrate at many sites but more superficially than typical sutures, distributing tension away from crucial nerve ends.
5) Improved mechanical fastening: Optionally, a tissue adhesive can be incorporated into the device to supplement the mechanical fastening of the microhooks.

The microhook nerve tape described herein can also essentially seal off the nerve coaptation from the surrounding body fluids, avoiding some of the problems associated with conduit lumen-nerve stump diameter mismatches. According to commercially available conduit manufacturers, contamination of the space between nerve stumps with blood should be avoided. The negative effects of conduit lumen-nerve stump diameter mismatch are well established and can be avoided by using the microhook nerve tape. An additional advantage of the microhook nerve tape/wrap-around concept is the broad distribution of "holding points."

Figure 6:
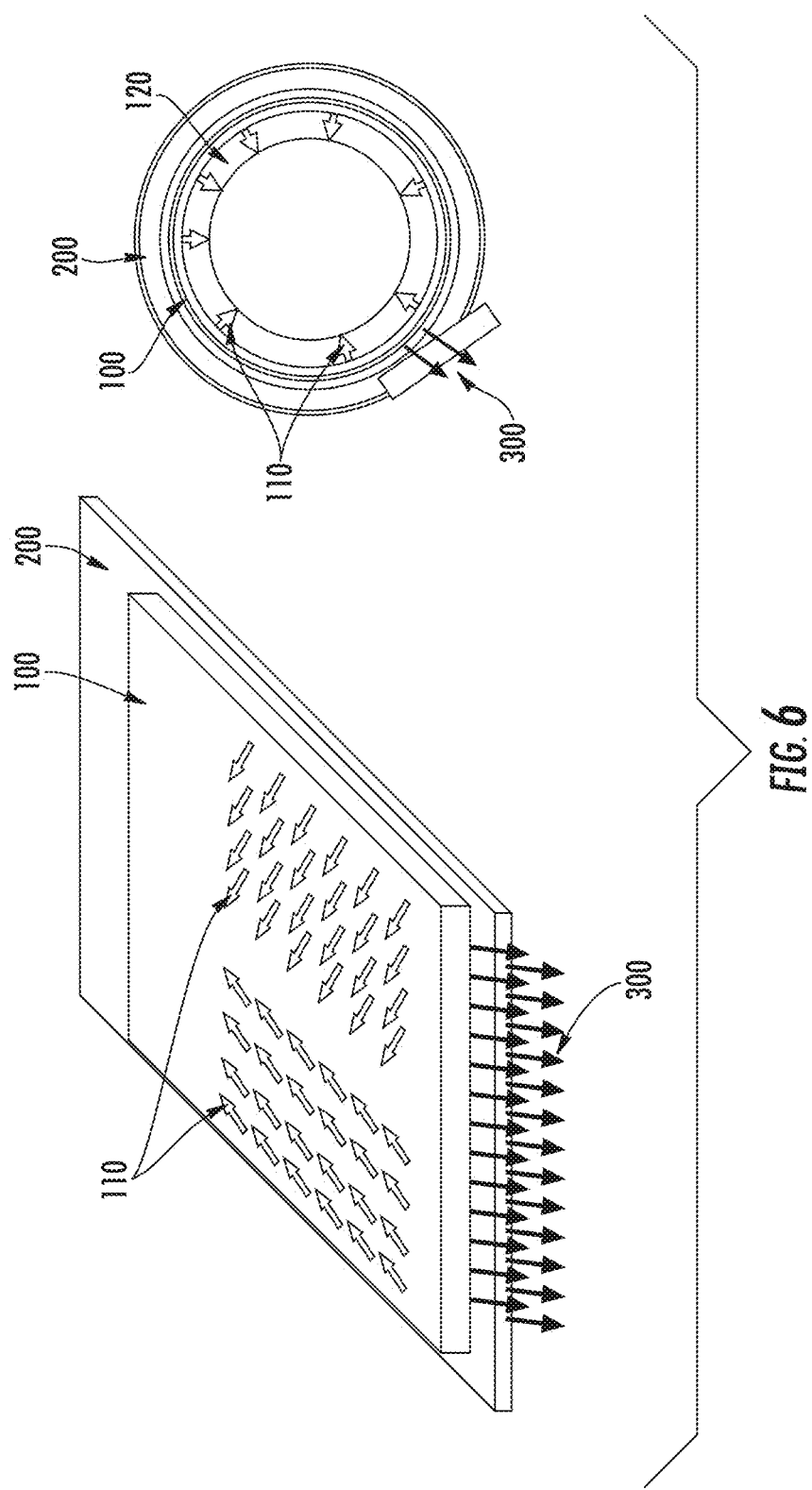
FIG. 6 illustrates another example nerve repair device, where the micro-protrusions 110 can attach to the nerve 120 and longer fastening hooks 300 separately attach to the flexible substrate 200 itself after wrapping, sandwiching, etc.
Figure 11A:
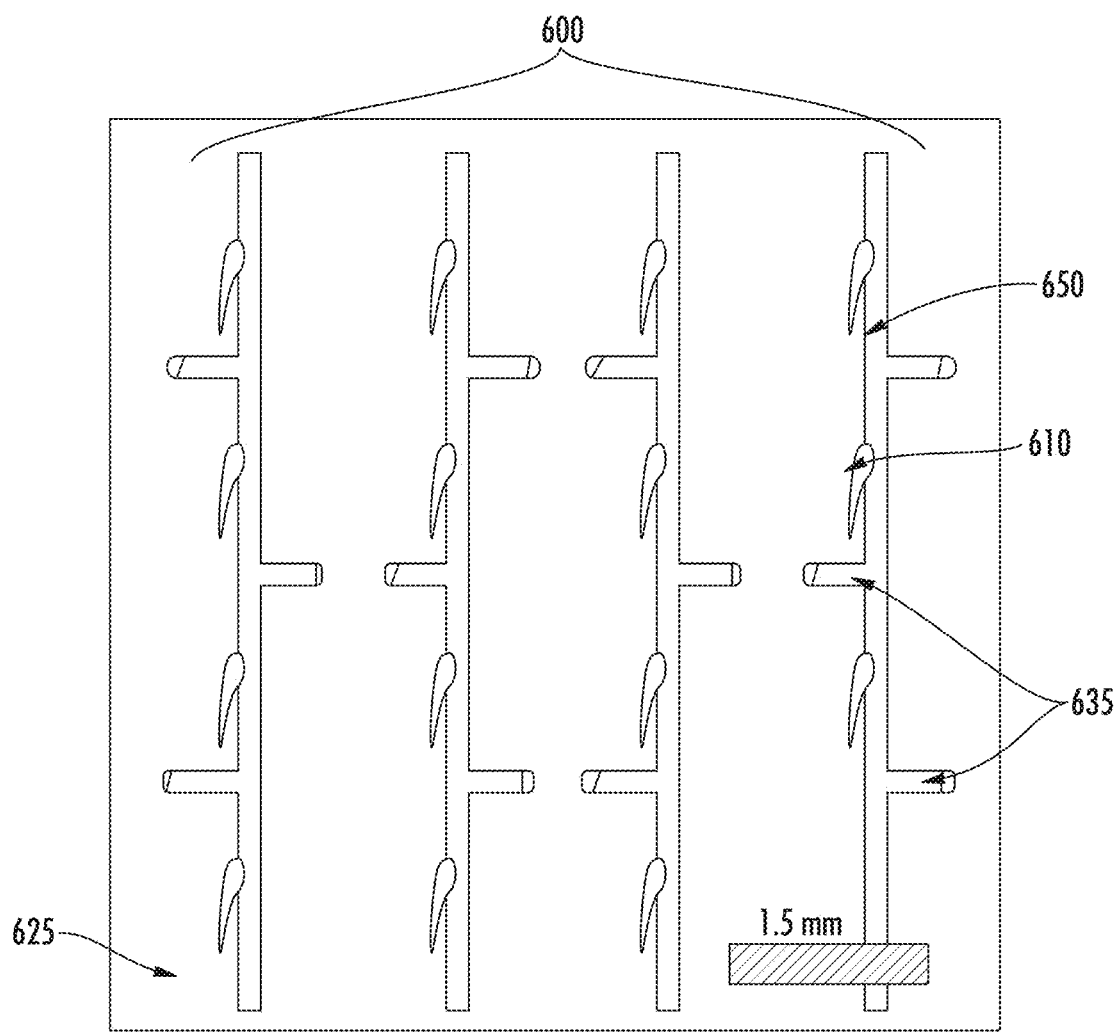
FIGS. 11A-11C illustrate another example nerve repair device.
Figure 11B:
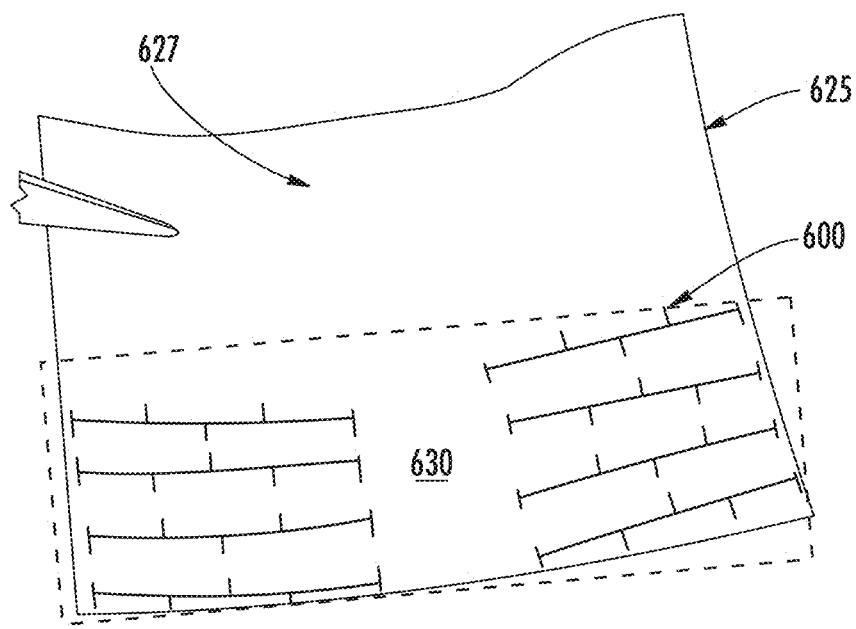
Figure 11C:
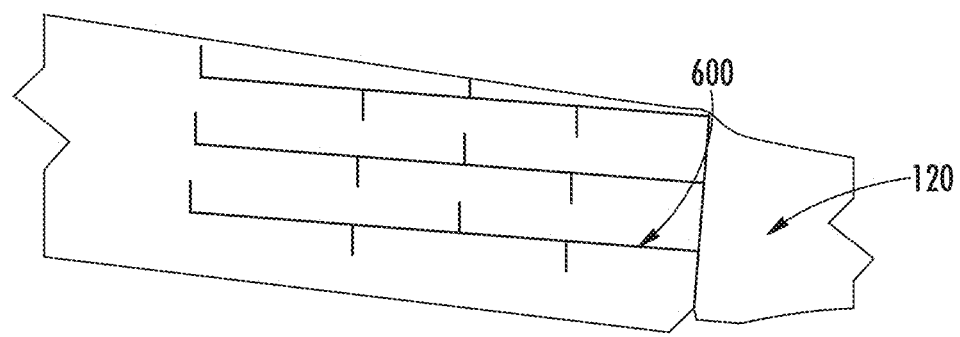

The device can include at least one flexible substrate (e.g., sometimes referred to as "flexible carrier layer"), where the support member (e.g., planar base 100 of FIG. 1) can be attached to the at least one flexible substrate (e.g., flexible substrate 200 as shown in FIGS. 1, 6, and 7). The flexible substrate can be at least one of a biocompatible, biodegradable, or bioresorbable material. In some implementations, the flexible carrier layer can be formed from a biologic material or processed biologic material including, but are not limited to, small intestine submucosa (SIS), collagen, amniotic, or other tissue. For example, the flexible substrate can be formed from small intestine submucosa (SIS). IAs described below, the micro-protrusions can form an array of micro-protrusions, where each of the micro-protrusions is independent. In this implementation, the flexible substrate, which is the backing material, provides mechanical strength and/or flexibility. The micro-protrusions can be integrated with the flexible substrate. Alternatively, the micro-protrusions can form an array of micro-protrusions, where one or more of the micro-protrusions is interconnected, e.g., by intersecting cross bridges as shown in FIGS. 4A-4B or by elongate strips as shown in FIGS. 11A-11C. The intersecting cross bridges or elongate strips form the support member. In this implementation, both the support member and the flexible substrate, which is the backing material, together provide mechanical strength and/or flexibility.

Examples backing material that is commercially available multi-laminar porcine extracellular matrix sheet (Axoguard, Axogen, Inc., Alachua, Fl) and collagen-based backing materials. The extracellular matrix sheeting has been in clinical use for several years and has a well-established record of biocompatibility. The material elicited a minimal inflammatory response and was readily incorporated into the mesoneurium (the connective tissue surrounding the nerve) when applied to a rabbit nerve. Clinically, it is already used as a scar barrier nerve wrap and as a suturable nerve connector.

The components of both the micro-protrusions (e.g., microhooks or microneedles) and flexible substrate (e.g., backing material) can be nonreactive and can maintain integrity for at least two to sixteen weeks, which are possible durations for a repaired nerve to regain similar tensile strength to an intact nerve. Optionally, the micro-protrusions and flexible substrate can potentially resorb or remodel (e.g., nonabsorbable conduits such as silicone have been associated with nerve irritation). The microhook nerve tape can also be economical, stable for transport, and have a reasonable shelf life.

A series of prototypes were fabricated and subjected to mechanical testing using human cadaver nerves. A number of representative prototypes and experimental results are described below.

Overall, experiments demonstrated that arrays of barbed microhooks were remarkably effective at mechanically fastening to the outer connective tissue layers of sample nerves, without damaging the deeper nerve elements. When embedded in a flexible substrate, the resulting "microhook nerve tape" can be used to efficiently coapt transected nerves and entubulate the repair site. Several benefits of the prototypes over conventional nerve repair techniques were demonstrated. The prototypes also confirmed the ability of metallic microhooks to firmly engage peripheral nerves and the ease of implantation of prototypes.

Figure 2:
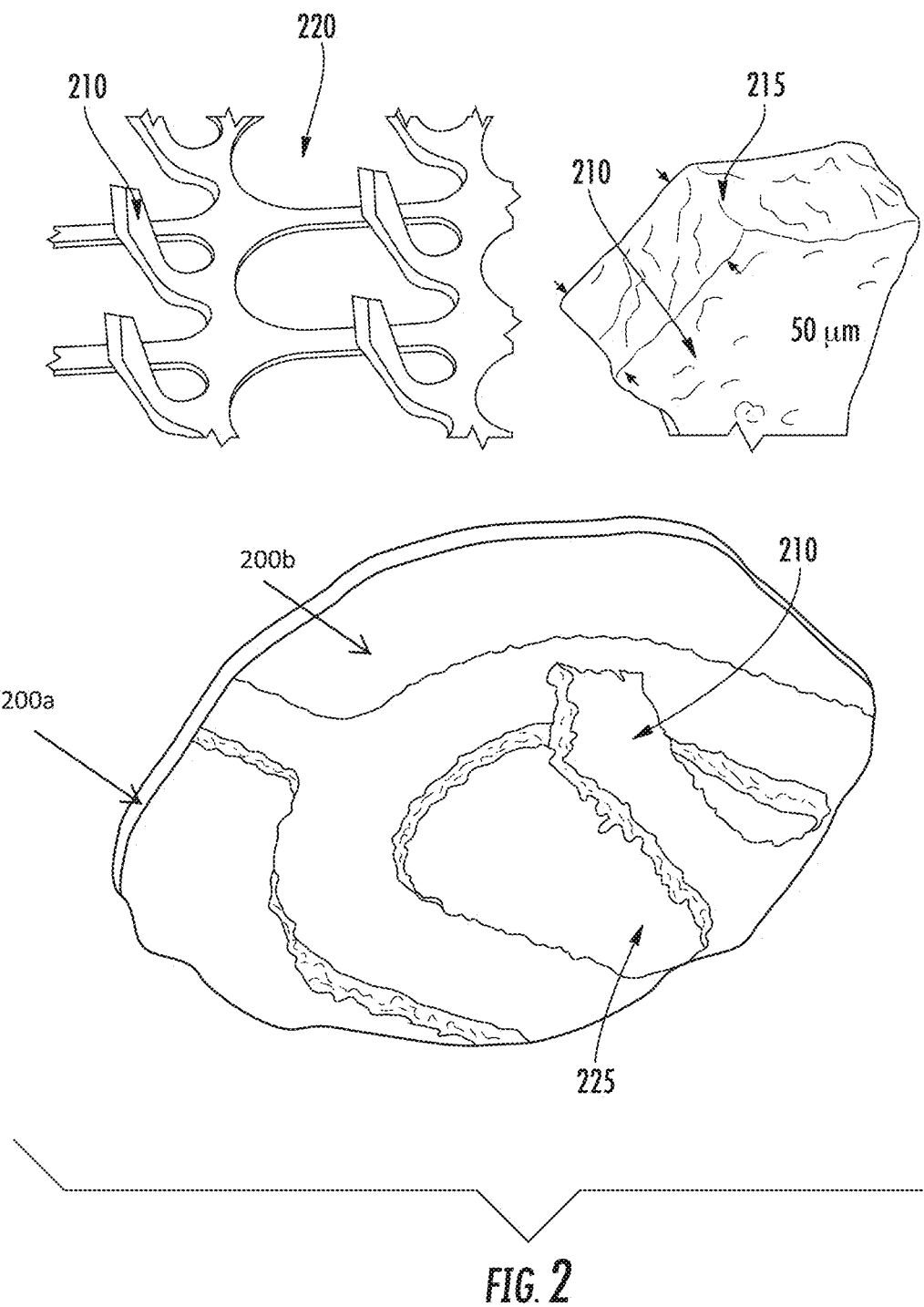
FIG. 2 illustrates example micro-protrusions that can be used in the device of FIG. 1.

Referring now to FIG. 2, example micro-protrusions 210 that can be used in the device of FIG. 1 is shown. In FIG. 2, the micro-protrusion 210 is a barbed-tipped microhook.

Microhook engagement of peripheral nerves: Metallic microhook structures were used to confirm that microhooks will engage peripheral nerves. A sheet of stainless steel (316L; 50 µm thickness) was laser micro machined (Resonetics Q Switched Nd:YIF laser) to have 500 µm length shanks in the planar foil as shown in FIG. 2. These barb-tipped shanks 215 were then manually bent out of the plane of the metal sheet with a stereoscope to form a monolithic microhook array structure 220.

Experiments with cadaver radial nerves (3-4 millimeters (mm) diameter) qualitatively characterized microhook attachment to neural tissue. The microhook array structure 220 was manually pressed onto the test nerves and pulled with forceps parallel to the nerve. Mechanical attachment and pull strength was judged as excellent. Also significant, the microhooks appeared to be penetrating only the outer connective tissue and epineurial nerve layers.

Figure 3A:
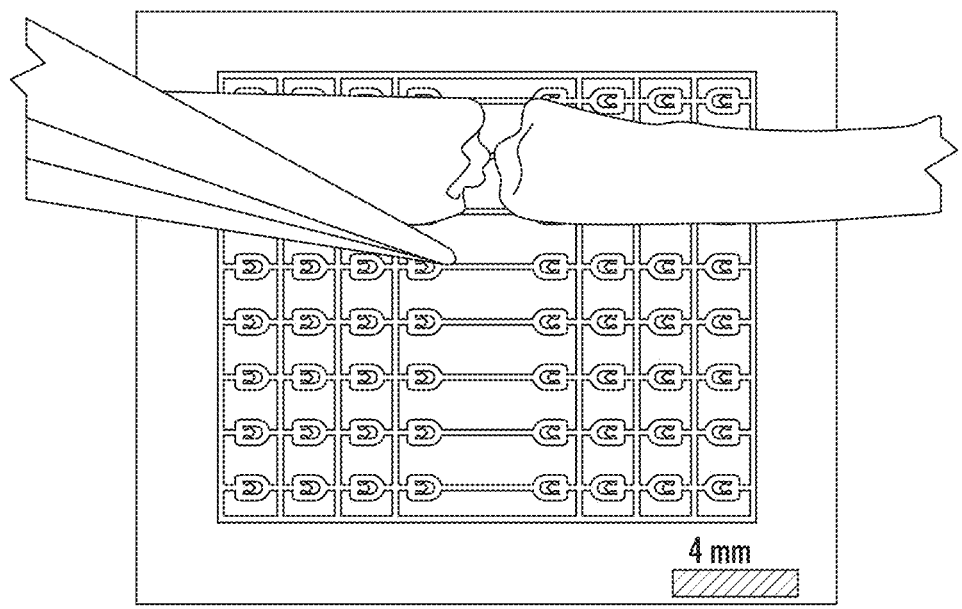
FIG. 3A illustrates a microhook array structure designed to distribute hooks in a "mesh" with thin, flexible connections between hooks.
Figure 3B:
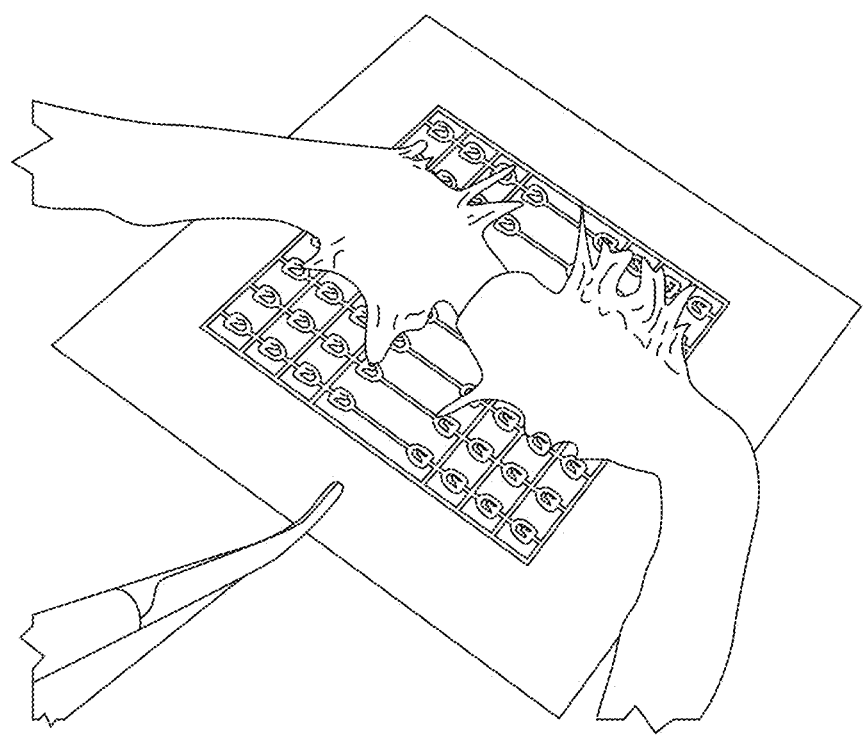
FIG. 3B illustrates a visual assessment of unwrapped repairs suggesting microhook attachment was limited to superficial nerve layers using the microhook array structure of FIG. 3A.

Functional prototype device development: The initial microhook array structure designs demonstrated excellent hold on the nerve, but were inflexible, preventing wrapping around nerve tissue. For other prototypes, the microhook array structure was redesigned to distribute hooks in a "mesh" with thin, flexible connections between hooks, which is shown by FIG. 3A. Microhooks were oriented in opposing directions on each side of the mesh to provide a pull force in opposite directions. The microhook mesh was encapsulated between two layers of 25 µm thick polyimide sheets (KAPTON polyimide film from E. I. du Pont de Nemours and Company of Wilmington, DE) to provide stability without impeding device flexibility. Microhook openings (e.g., microhook openings 225 of FIG. 2) in the top sheet were defined with a $CO_2$ laser (Gravograph LS 500XL), and sheets were bonded together using an acrylic adhesive with the mesh layer in between. In FIG. 2, the top sheet (e.g., a first flexible carrier layer) is labeled with reference number 200a, and the bottom sheet (e.g., a second flexible carrier layer) is labeled with reference number 200b. The microhook array structure 220 of FIG. 2 is sandwiched between the top sheet 200a and the bottom sheet 200b. Mechanical hold was acceptable in qualitative cadaver nerve testing. Visual assessment of unwrapped repairs suggested microhook attachment was limited to superficial nerve layers, which is shown by FIG. 3B.

Prototype evaluation: Four prototype devices were fabricated for comparison with microsutures in a simulated nerve repair using cadaver nerves (4-5 mm diameter) by an experienced microsurgeon, who took an average of 1 minute and 58 seconds per microhook nerve repair compared to 5 minutes and 55 seconds for microsuture repair (e.g., four 8-0 nylon sutures with an operating scope as shown in Table 1).

TABLE 1

| | Implant time (min) | | Pull force (g) | |
|---|---|---|---|---|
| | µ-hooks | 4 µ-sutures | µ-hooks | 4 µ-sutures |
| 1 | 2:05 | 5:15 | 106.6 | 368.4 |
| 2 | 2:22 | 6:37 | 145 | 416.5 |
| 3 | 1:36 | 5:54 | 97.6 | 402.2 |
| 4 | 1:50 | 5:11 | 197.7 | 389.1 |
| x̄ | 1:58 | 5:55 | 136.7 | 394.1 |

Subsequent biomechanical testing (Instron, 1321) revealed microhook nerve tape repairs were stable against tensile force of up to 198 g. Though the microhook nerve tape prototypes withstood less force than the four-suture repairs, the microhook nerve tape provided repair strengths in the range of two sutures (180 grams (g)). Traditionally, for nerve coaptations that require more tension than can be offset by a single 8-0 suture, a graft or other alternative to direct coaption is prescribed. This is due to tension induced inhibition of axon regeneration. As a result, the reduced tensile strengths of the microhook repairs are acceptable.

Referring now to FIGS. 4A and 4B, example devices for repairing a nerve are shown. The devices include a support member 100 including a plurality of micro-protrusions 110 (e.g., microhooks, microneedles, etc.). As described herein, the support member 100 can be formed of a metal (e.g., a metallic support member) in some implementations. For example, the metallic support member can optionally be formed form Nitinol or other superelastic alloy. The micro-protrusions 110 can be bent out of plane from the support member 100 in a direction of a first axis or a second axis of the support member 100. In FIGS. 4A and 4B, the nerve to be repaired is assumed to extend along the first axis. In other words, the longitudinal axis of the nerve is substantially parallel to the first axis. Referring to FIG. 4A, the micro-protrusions 110 can be bent out of plane from the support member 100 in the direction of the first axis, where the first axis substantially corresponds to an axis along a length of the nerve (i.e., along a longitudinal axis of the nerve). This is sometimes referred to below as bending out of plane in the direction of the vertical axis. Referring now to FIG. 4B, the micro-protrusions 110 can be bent out of plane from the support member 100 in the direction of the second axis, where the second axis substantially corresponds to an axis following a circumference of the nerve 120. This is sometimes referred to below as bending out of plane in the direction of the horizontal axis.

The micro-protrusions 110 can form an array of interconnected micro-protrusions 110. In some implementations, the micro-protrusions 110 are embedded in a flexible carrier layer, which can be a flexible substrate or backing material, i.e., a plurality of individual micro-protrusions 110 embedded in a flexible substrate. Optionally, in some implementations, the device includes a plurality of flexible substrates, and the micro-protrusions 110 are sandwiched (e.g., laminated) between the plurality of flexible substrates. As described herein, the backing material provides the mechanical strength and/or flexibility in this implementation. In some implementations, the flexible substrate can be formed from a biologic material or processed biologic material including, but are not limited to, small intestine submucosa (SIS), collagen, amniotic, or other tissue. In other implementations, the micro-protrusions 110 can be interconnected via a plurality of intersecting cross bridges 150A, 150B (collectively referred to herein as "intersecting cross bridges 150"). In this implementation, the intersecting cross bridges 150 form the support member 100. Cross bridges 150A are sometimes referred to herein as horizontal cross bridges, and cross bridges 150B are sometimes referred to herein as vertical cross bridges. Each of the intersecting cross bridges 150A, 150B can be an elongate strip having micro-protrusions 110 extending therefrom. As described herein, the support member 100 (and optionally the backing material) provide the mechanical strength and/or flexibility in this implementation. This disclosure contemplates that widths of the intersecting cross bridges 150 and/or spaces between the intersecting cross bridges 150 can optionally be configured to optimize at least one of strength or flexibility of the support member 100. As described herein, the support member 100 can be designed to minimize kinking of the device. In some implementations, cross bridges 150 extending in a direction substantially corresponding to an axis following a circumference of the nerve are not provided in proximity to a repair site. For example, as shown in FIGS. 4A and 4B, horizontal cross bridges 150A are absent in a region in proximity to a repair site 130. As described herein, this can minimize kinking in the device. The support member 100 can optionally further include at least one extending feature 160 configured to at least partially surround a micro-protrusion 110. The extending feature 160 can provide lateral support for the micro-protrusion 110. As described herein, the support member 100 can optionally be formed from Nitinol to minimize kinking of the device. The device can optionally be configured for drug delivery or cell transplantation, for example, the support member 100 and/or flexible carrier layer can be configured for drug delivery or cell transplantation such as stem-cell seeding to enhance regeneration. Alternatively or additionally, the device can be configured to apply an electrical stimulus to the nerve and/or record electrical activity from the nerve, for example, via one or more of the micro-protrusions 110.

Referring now to FIG. 4A, the micro-protrusions 110 of the device bend out of plane from the support member 100 in the direction of the vertical axis (i.e., the first axis), which is the same axis along which nerve tension is applied after the constructs are implanted to coapt severed nerve ends. The typical nerve tension after repair can torque the micro-protrusions 110 along the same direction that they were originally rotated out of plane from the support member 100. Further bending along this axis may result in the tip of a micro-protrusion 110 extending further away from the support member 100. This may translate into increased "effective penetration depth" into the nerve interior. For example, a 500 micrometer (μm) length micro-protrusion bent 30° out of plane would have a tip that extends at most 250 μm (i.e., 500*sin)(30°) from the base plane of a two-dimensional (2D) substrate. If this bending angle is maintained after wrapping the 2D mesh with bent micro-protrusions around a nerve, then the micro-protrusion would extend no more than 250 μm into the interior of the nerve. If nerve tension pulls on the micro-protrusion and increases the bending angle to, for example, 45°, then the tip of the micro-protrusion would then penetrate to a depth as great as 354 μm (500*sin)(45°) into the nerve. Increased tension and flexing of micro-protrusions may even lead to micro-protrusions pointing in the wrong direction, which would severely limit their effectiveness in holding the repair site together.

Referring now to FIG. 4B, the micro-protrusions 110 are bent out of plane in the direction of the horizontal axis (i.e., the second axis). In this configuration, the micro-protrusions 110 are more resistant to nerve tension directed along the vertical axis. There are several advantages of this configuration. For example, the effective angle of the bent micro-protrusions are determined by the 2D design, so all micro-protrusions can be more easily translated out of plane to the same effective angle. The resulting minimized variation of micro-protrusion bending angles means that the micro-protrusions may be more easily inserted into tissue. Once inserted into tissue, the micro-protrusions have greater resistance to bending and tensile strength along the vertical axis, the same axis along which nerve tension will be typically distributed. Also, because the micro-protrusions are more resistant to bending along the vertical axis, the micro-protrusions are more resistant to bending in such a way that would increase their effective penetration depth.

The results of Instron testing with cadaveric nerves to assess attachment strengths of the device of FIGS. 4A and 4B are shown in Table 2. A parameter sweep of microhook lengths were tested.

TABLE 2

| FIG. 4B: different microhook lengths, where 100% represents 500 μm length | Pull Force (g) at failure in cadaver nerve testing |
| --- | --- |
| 100% | 708.7 |
| 90% | 458.9 |
| 80% | 280.4 |
| 70% | 305.9 |
| 60% | 295.7 |
| 50% | 377.3 |
| 100% | 234.5 |
| 100% | 642.4 |

Referring now to FIGS. 11A-11C, another example device for repairing a nerve is shown. As shown in FIGS. 11A and 11B, the device can include a metallic support member 600 including a plurality of micro-protrusions 610 on a surface thereof. For example, the micro-protrusions 610 can be configured to attach to the outer epineurium without penetrating into the interior portions of the nerve where the axons reside, which minimizes atraumatic penetration. For example, the micro-protrusions 610 can be sized and shaped to pierce the outer epineurium but without piercing a fascicle (i.e., bundle of axons). Optionally, the micro-protrusions 610 can be sized and shaped to pierce the outer epineurium without piercing the perineurium. Alternatively or additionally, in some implementations, the micro-protrusions 610 can be sized and shaped to penetrate the nerve to a depth between about 100 μm and about 1 mm, and optionally to penetrate the nerve to a depth between about 200 μm and about 500 μm. Additionally, the device can include a flexible carrier layer 625. As described herein, the flexible carrier layer 625 can be formed from biocompatible, biodegradable, or bioresorbable material. In some implementations, the flexible carrier layer 625 can be formed from a biologic material or processed biologic material including, but are not limited to, small intestine submucosa (SIS), collagen, amniotic, or other tissue. For example, the flexible carrier layer 625 can be formed from small intestine submucosa (SIS). In some implementations, the metallic support member 600 can be attached to or bonded to a surface of the flexible carrier layer 625. Alternatively, the metallic support member 600 can be at least partially embedded within the flexible carrier layer 625. Optionally, in some implementations, the device includes a plurality of flexible carrier layers, and the metallic support member 600 is sandwiched (e.g., laminated) between the plurality of flexible carrier layers.

The flexible carrier layer 625 can be a substantially two-dimensional sheet as shown in FIG. 11B. In this way, the flexible carrier layer 625 and metallic support member 600 can serve as nerve tape, e.g., the nerve tape can be wrapped on or otherwise applied to a repair site as described herein. As shown in FIG. 11B, a wrapping portion 627 of the flexible carrier layer 625 can be provided for adequately closing the device. The wrapping portion 627 can be configured for self-closure, e.g., without separate mechanical closing mechanism and/or adhesive. In some implementations, the micro-protrusions 610 are not provided in the wrapping portion 627. In other implementations, both the micro-protrusions 610 and the metallic support member 600 are not provided in the wrapping portion 627 as shown in FIG. 11B. By using the wrapping portion 627, a separate mechanical closing mechanism is not necessary to close the device. This disclosure contemplates that a separate mechanical closing mechanism may pose risk of tissue irritation, nerve impingement or constriction. The wrapping portion 627 (e.g., flap of SIS or other biologic material) can adequately close and seal a tubular construct without incidences of unwrapping. The wrapping portion 627 can be optimized by altering the thickness or number of laminated sheets, or surface characteristics, or other processing methods. This disclosure contemplates that such optimization may decrease material bulk and further increase adherence of the closure leaf as it wraps.

In some implementations, the device can be configured to entubulate a repair site on a nerve 120, for example, as shown in FIG. 11C. The repair site can be a coaptation site, and the device can entubulate the repair site. As noted above, it should be understood that a coaptation site is provided only as an example and that this disclosure contemplates using the device to repair other nerve damage including, but not limited to, nerve gap repair, allograft, autograft, and/or xenograft. In other implementations, the device can be configured to sandwich the repair site (e.g., as shown by the devices of FIGS. 7 and 8).

As shown in FIGS. 11A and 11B, the metallic support member 600 can include a plurality of elongate strips 650. The elongate strips 650 can be free floating (e.g., not connected to one another) within the flexible carrier layer 625. The elongate strips 650 can extend in a direction that substantially corresponds to an axis along a length of the nerve (i.e., along a longitudinal axis of the nerve). Additionally, the micro-protrusions 610 can extend from the elongate strips 650 as shown in FIG. 11A. In some implementations, the micro-protrusions 610 can be bent out of plane from the support member 600 in the direction that substantially corresponds to an axis along a length of the nerve (i.e., along a longitudinal axis of the nerve). This is sometimes referred to herein as bending out of plane in the direction of the vertical axis. This is similar as described with respect to FIG. 4A. In other implementations, the micro-protrusions 610 can be bent out of plane from the support member 600 in the direction that substantially corresponds to an axis following a circumference of the nerve. This is sometimes referred to herein as bending out of plane in the direction of the horizontal axis. This is similar as described with respect to FIG. 4B. When the micro-protrusions 610 bend out of plane in the direction of the horizontal axis, the micro-protrusions 610 are more resistant to nerve tension directed along the vertical axis, which has advantages as discussed herein. Alternatively or additionally, the elongate strips 650 can include one or more projecting members 635. The projecting members 635 can provide lateral support for the micro-protrusions 610. For example, when the metallic structural member 600 is integrated with the flexible carrier layer 625, the projecting members 635 can stabilize the micro-protrusions 610. In one implementation, as shown in FIG. 11A, the projecting members 635 extend in the direction that substantially corresponds to an axis following a circumference of the nerve (i.e., horizontal axis) on either side of the elongate strips 650. In other words, in contrast to FIGS. 4A and 4B, the metallic support member 600 is not cross connected. It should be understood that the projecting members 635 can be have other shapes (e.g., circular, curved, square, rectangular, etc.) than as shown in the example of FIG. 11A. As described above, the projecting members 635 can be sized and shaped to provide lateral support. The projecting members 635 can increase the mechanical strength of the metallic support member 600.

Optionally, as shown in FIG. 11B, the micro-protrusions 610 can include a first group of micro-protrusions and a second group of micro-protrusions, for example, on opposite sides of a "demilitarized zone," or region corresponding to a repair site 630. To create the "demilitarized zone," a gap can be provided in the elongate strips, which forms a plurality (e.g., 2 in FIG. 11B) of islands of micro-protrusions. Optionally, the first and second groups of micro-protrusions can be oriented to face each other as described herein. In another implementation, the elongate strips 650 can extend through the repair site 630. Optionally, micro-protrusions 610 are not provided along the elongate strips 650 in this region, i.e., in the "demilitarized zone." This disclosure contemplates that elongate strips spanning the repair site 630 can improve device integrity. In some cases, for example at relatively high tensions, one or more portions of the metallic support member 600 may tear from the flexible carrier layer 625 near the repair site 630. With elongate strips extending through the repair site 630, this failure mode can be minimized and/or eliminated.

Referring now to FIG. 15, another example device for repairing a nerve is shown. As shown in FIG. 15, the device can include one or more support members 700, each support member including a micro-protrusion 710 on a surface thereof. Optionally, as described herein, the support members 700 can be formed from a metal such as a superelastic alloy (e.g., Nitinol). For example, the micro-protrusions 710 can be configured to attach to the outer epineurium without penetrating into the interior portions of the nerve where the axons reside, which minimizes atraumatic penetration. For example, the micro-protrusions 710 can be sized and shaped to pierce the outer epineurium but without piercing a fascicle (i.e., bundle of axons). Optionally, the micro-protrusions 710 can be sized and shaped to pierce the outer epineurium without piercing the perineurium. Alternatively or additionally, in some implementations, the micro-protrusions 710 can be sized and shaped to penetrate the nerve to a depth between about 100 μm and about 1 mm, and optionally to penetrate the nerve to a depth between about 200 μm and about 500 μm. Additionally, the device can include a flexible carrier layer 725. As described herein, the flexible carrier layer 725 can be formed from biocompatible, biodegradable, or bioresorbable material. In some implementations, the flexible carrier layer 725 can be formed from a biologic material or processed biologic material including, but are not limited to, small intestine submucosa (SIS), collagen, amniotic, or other tissue. For example, the flexible carrier layer 725 can be formed from small intestine submucosa (SIS). In some implementations, the support member 700 can be attached to or bonded to a surface of the flexible carrier layer 725. Alternatively, the support member 700 can be at least partially embedded within the flexible carrier layer 725. Optionally, in some implementations, the device includes a plurality of flexible carrier layers, and the support member 700 is sandwiched (e.g., laminated) between the plurality of flexible carrier layers. Alternatively or additionally, the support member 700 can include one or more projecting members 735. As shown in FIG. 15, the projecting members 735 extend on either side of the support member 700. In other words, similar to FIGS. 11A-11C, the support member 700 is not cross connected with other support members. In contrast to FIGS. 11A-11C, each support member 700 includes only a single micro-protrusion 710. The projecting members 735 can increase the mechanical strength of the support member 700. As described above, the projecting members 735 can provide lateral support for the micro-protrusions 710. For example, when the structural member 700 is integrated with the flexible carrier layer 725, the projecting members 735 can stabilize the micro-protrusions 710. It should be understood that the projecting members 735 can be have other shapes (e.g., circular, curved, square, rectangular, etc.) than as shown in the example of FIG. 15.

Microhook Design Parameters

Individual micro-protrusion design parameters: As described herein, micro-protrusions can include, but are not limited to, microhooks, microneedles, etc. A micro-protrusion is any structural protrusion intended to mechanically interface with contacted tissues. A microhook is only an example micro-protrusion. It should be understood that the discussion of microhooks below applies to other types of micro-protrusions including, but not limited to, microneedles. Microhooks can be designed to have certain characteristics. For example, microhooks can be designed to easily penetrate the desired tissue, such as the superficial epineurial tissues of a nerve. Microhooks can be designed for minimal penetration of undesired tissues, such as the interior endoneurium or fascicles of a nerve. Microhooks can be designed to resist undesired pulling out from the nerve after penetration. Microhooks can be designed so that they can be purposefully removed from the nerve without causing excessive tissue damage. Microhooks can be designed to resist bending or breaking during mechanical loading. Microhooks can be designed so that a strength-to-material ratio is high, to minimize the amount of material (e.g., weight, surface area, volume, etc.) that is used. Microhooks can be designed for short and long term biocompatibility.

To achieve these types of characteristics, microhook design parameters can vary microhook material, shape, geometry, length, and density. These parameters can be balanced to optimize potentially competing goals such as strength, flexibility, minimization of material, and ease of attachment to epineurial tissue.

Microhooks can be designed for specific characteristics. For example, microhooks can be designed to facilitate penetration into desired tissues. This can be accomplished with a tip of appropriate properties, such as hardness, sharpness, or a small substrate thickness. For example, thinner tips may penetrate tissue easier. Sharper tips may also penetrate tissue easier. Microhooks can also be designed to resist pulling away from tissues. For example, microhooks can have ridges to increase mechanical stability, barbs to reduce pullout from tissue once inserted, angles to hold outer layers of connective tissue without penetrating too deeply, curves to ease with insertion placement and hold, serrated edges to offer multiple grab points, spikes, raised features, or other 2D or 3D geometries to resist pulling away from tissues. Microhooks can be designed for an optimized balance of resistance to pulling away from tissues and minimization of damage when pulling away is desired and forced. For example, a small barb can prevent microhooks from pulling away from tissues due to normal tensions or body motions, but the barb can be small enough that the surgeon could remove the microhook when repositioning the construct without "shredding" tissues or causing undue tissue damage. Microhooks can have multiple barbs in different directions, or may look like a "fractal" or "fern" shape to increase the number of grab points to resist removal once inserted.

Microhooks can be designed to optimize the balance between the strength of hold for each microhook and the level of invasiveness to relevant body tissues. For example, shaft lengths can be selected such that microhooks penetrate sufficiently into epineurial tissues to form a strong mechanical hold, without penetrating deeper into the interior of the nerve, where axons reside. For example, shaft lengths can be 1 mm or less, or 500 µm or less, or 100 µm or less. In some implementations, the effective penetration depth can be between about 100 µm and about 1 mm, and optionally t between about 200 µm and about 500 µm. The effective penetration depth is the amount by which the micro-protrusions (e.g., microhooks) penetrate into a nerve. For example, a 500 micrometer (µm) length micro-protrusion bent 30° out of plane would have a tip that extends at most 250 µm (i.e., 500*sin(30°) from the base plane of a two-dimensional (2D) substrate, i.e., the effective penetration depth is 250 µm. It should be understood that other layers, for example, a flexible carrier layer or flexible substrate into which the micro-protrusions are incorporated can reduce the effective penetration depth. For example, a 50 µm thick layer of SIS can reduce the effective penetration depth of the 500 µm micro-protrusions in the example above to 200 µm. The thickness of the support member (e.g., planar base 100 of FIG. 1 and/or backing material such as flexible substrate 200 of FIG. 1) can be selected to give mechanical strength to the microhooks without being so thick as to be overly bulky or invasive. For example, a metallic substrate, such as stainless steel, can be selected to be about 50 microns thick. Thicknesses can range from several millimeters or more down to 10 microns or less. The geometries of the microhooks can also be tuned for desired characteristics. For example, the microhook widths can be selected to impart strength and resistance to bending back of the microhooks under tension.

Microhooks can be bent or formed or extended at desired angles from the planar base (e.g., planar base 100 of FIG. 1), e.g., from −180 degrees to 180 degrees. For example, a 30 degree angle can be selected to facilitate penetration and resistance to microhook bending under tension. Microhook angles can be different for different microhooks. Angles can be chosen to resist opening of the repair site.

Microhooks and arrays of microhooks can have varied design parameters for desired characteristics. For example, microhooks can be made of different materials. For example, polymeric, metallic, ceramic, glass, or silicon materials can be used. Metallic materials, including stainless steel, titanium, Nitinol, platinum, iridium, platinum iridium, or magnesium can be used. Preliminary experiments have been performed using biocompatible 316L Stainless Steel, which has shown to be well tolerated for long-term contact with nervous tissue.

Biodegradable materials: Materials with biodegradable, bioresorbable, or similar properties can be used. This disclosure contemplates that the planar base and/or backing material can optionally be made from biodegradable, bioresorbable, etc. materials. For example, materials like PLGA, PLLA, PLLA/PLGA, collagen, chitosan, small intestine submucosa (SIS), magnesium can be used. Biodegradable metals such as magnesium and zinc, have been shown to have neutral or even pro-regenerative effects during biodegradation. These materials can allow for initial micro-protrusion penetration, and/or mechanical fastening/fixturing of tissues followed by a dissolving, biodegrading, or tissue resorption of the materials over time.

Materials with various mechanical properties can be selected. For example, some "shape memory alloys" such as alloys of Nickel-Titanium ("Nitinol") "remember" their pre-formed shape and can return to it during heating. These materials also display properties of pseudoelasticity (sometimes referred to as "superelasticity") and can be deformed by strains as high as 10% and still return their original state. Superelastic alloys can be resistant to kinking or creasing, where a sharp angle bend or crease may irreversibly close off the channel formed by entubulation. The shape memory properties of these materials can also be valuable and exploited. For example, microhooks may bend into a different configuration when implanted into body tissues. The temperature of the body tissues may cause microhooks to penetrate into the tissue, or for the construct to wrap or curl around the tissues, such as a nerve. Different combinations of materials can be used. For example, polymeric microhooks can have ceramic tips to provide a hard tip that can more easily penetrate tissues. A temporarily hard or sharp tip can be formed through a variety of means, with the intended purpose of achieving initial tissue penetration before dissolving or degrading. Microhooks can be formed by coating water-soluble crystals in polymer to provide temporary hardness or sharpness. After dissolving the crystals, penetrated microhooks remain in the tissue.

Arrays of Microhooks:

Microhooks can be arranged in an array according to different designs or techniques. For example, microhooks can be distributed across a support structure (e.g., planar base 100 of FIG. 1 or metallic support member 100 of FIGS. 4A-4B or metallic support member 600 of FIGS. 11A-11C). The support structure can be patterned in a mesh or grid of microhooks, with square, diamond, round or different shaped and sized openings in the mesh. This mesh or grid can be designed to optimize flexibility when wrapped around a nerve. Characteristics of the mesh can include the placement of individual microhooks on a mesh. Microhooks can be at the intersection of the mesh, along structural elements (e.g., cross bridges and/or elongate strips as described herein) or at different angles to structural elements. Microhooks can be spaced on a regular grid array, or offset. Meshes of microhooks may have the area near the repair site free of microhooks (e.g., a demilitarized zone as described herein) and open for less intrusion into the repair site and greater clarity when aligning the two ends.

A microhook array based on a mesh, grid, or lattice type structure can have an advantage of increased strength. Vertical and/or horizontal cross bridges (e.g., cross bridges 150A, 150B of FIGS. 4A and 4B) and/or elongate strips (e.g., elongate strips of FIGS. 11A-11C) can provide excellent tensile strength. Design parameters can be adjusted to optimize this strength while also maximizing flexibility of the construct (e.g., especially in the case of a wrapping embodiment) and/or minimizing the amount of material used to create the array.

Experiments have revealed that it is desirable that the mesh not kink, crease, or crush irreversibly, especially under the forces that the mesh can be expected to encounter within the body after implantation. One option for minimizing kinking in, say a metal like stainless steel that has the potential to kink, can be thinning, minimizing, or eliminating cross bridges within the mesh. For example, horizontal cross bridges of the device can be eliminated while leaving vertical cross bridges intact (e.g., as shown by removing horizontal cross bridges 150B near the repair site 130 in FIGS. 4A and 4B). Additionally, elongate strips (e.g., elongate strips of FIGS. 11A-11C) extending only in the direction that substantially corresponds to an axis along a length of the nerve (i.e., along a longitudinal axis of the nerve) can be provided. Eliminating the horizontal cross bridges can reduce the tendency for radial kinking of the wrapped device. The vertical cross bridges would still provide axial strength and resistance to nerve tension along the vertical axis.

Another strategy to minimize this potential for kinking is to use materials with a natural mechanical resistance to kinking for the mesh, or for the cross bridges of the mesh. For example, Nitinol is a material commonly used in tubular form for coronary stents, and its natural material properties resist kinking. In regards to other desired mechanical properties of the device, Nitinol's mechanical properties may not be optimal. For example, a 2D Nitinol device can have an undesired tendency to spring open after being rolled up into tubular form. To counter this, the horizontal cross bridges of the device can be thinned, minimized, or eliminated. In the case of reduced or eliminated horizontal cross bridges, the vertical cross bridges can have an increased tendency to rotate along their long, vertical axis. Incorporating horizontal extending features (e.g., horizontal extending feature 160 of FIG. 4A) can help prevent this rotation, especially once the mesh is incorporated into a backing material. As an example, "windows" encircling each microhook could provide this lateral support, and also provide support for bending each microhook out of plane.

Heat-forming the mesh to have a natural curve or a shape-memory aspect can also address undesired kinking, or undesired "springiness" and resistance towards wrapping the nerve during entubulation. The process of bending microhooks into their permanent bent-out-of-plane configuration can also be more difficult with Nitinol, precisely due to its ability to resist kinking. Heat-forming techniques or shape-memory techniques can be used to enable bending of the microhooks.

It can be desirable to design different portions of the mesh with different materials, geometries, or thicknesses for different mechanical properties. For example, thinning portions of the device can be advantageous at the microhook tips to increase sharpness. Thinning portions of the device at the cross bridges of the frame can increase flexibility and reduce the potential for kinking of the device as described above. Varied thicknesses allow load-bearing portions of the frame such as microhook shanks, bases, and supporting material, to remain relatively thick for maximized strength. Elsewhere, the device can be thinned for increased sharpness, flexibility, and/or resistance to kinking.

The mesh can be constructed from multiple materials. For example, the microhooks can be made of metal for the desired strength and sharpness. Elsewhere, the mesh can be made from polymer for increased flexibility, stretchability, or biodegradability. Microhooks can be made from one metal, such as stainless steel, which can be more easily bent at desired angles, and elsewhere the device can be made from another metal, such as Nitinol, which is flexible and resists kinking.

Strings of microhooks (e.g., elongate strips of FIGS. 11A-11C) could be made instead of a mesh. The strings of microhooks can span the repair site (along the "vertical" axis referred herein) and provide increased mechanical strength to the repair site by coupling the needles on either side of the gap to each other. Strings of microhooks also reduce the amount of material being implanted and may reduce kinking of the construct at the repair site. Strings of microhooks could be made by removing many of the support structures from a mesh. Alternatively, strings of microhooks can be made on a nylon or metal filament and sewed into a backing material. Alternatively, strings of microhooks can be made on a substrate and twisted to have microhooks pointing in all directions around a central axis.

Microhooks can be tuned for parameters such as strength and or flexibility. The design parameters shown in Table 3 below can affect the microhook yield strength, mesh flexibility, and attachment properties. Design parameters for the microhook meshes can be selected to find the optimal balance of strength and flexibility, while minimizing microhook penetration to the depths of axon-containing fascicles.

TABLE 3

| Microhook parameter | Sample range |
| --- | --- |
| Shank length | 100-800 μm |
| Shank width | 50-150 μm |
| Array density | .25-2 per mm$^2$ |
| Metal thickness | 25-100 μm |
| Hook undercut | −45° to 45° |
| Mesh row width | 25-200 μm |
| Mesh col. width | 25-200 μm |

Experiments have revealed the desirability of a highly flexible structure that is able to conform tightly to the nerve when applying to or wrapping around the nerve. A highly flexible, conformable structure resulted in superior microhook penetration and engagement. These flexible structures were achieved by reducing or minimizing horizontal cross bridges (e.g., cross bridges 150A, 150B of FIGS. 4A and 4B or elongate strips of FIGS. 11A-11C) and using thin 2D substrates (e.g., planar base 100 of FIG. 1), such as 50 micron or less stainless steel or Nitinol.

Manufacturing strategies: While laser machining and etching are established techniques that scale to manufacturing quantities, the microhook structures are be bent out of plane (2D to 3D) to create the hook-like structures. It is desirable to automate such bending (e.g., as opposed to manual bending) to produce the devices described herein. Stamping and/or Electron Discharge Machining (EDM) can be used in an automated stamping system for the microhook arrays, for example.

To develop and produce reliable and cost-effective devices, several fabrication strategies may be used. Laser micromachining techniques can be used to fabricate variations for prototype optimization. Meshes of biocompatible metal can be refined to identify the optimal/critical parameters to balance microhook yield strength with structural flexibility. For example, cross bridges of the microhook array can be thinned down into microscale filaments with high flexibility but great tensile strength to ensure that the gap distance at the repair site remains uniform.

Dissimilar materials can be bonded with adhesives, laser or microwelding, mechanical attachments such as clips, chemical techniques, or a variety of other means. In one implementation, a horizontal and vertical lattice of a material of a given thickness can be microwelded or otherwise bonded to a diagonal lattice of the same or different material, with the same or different thicknesses. Undesired cross bridges of one material type can then be removed via cutting, stamping, lasering, micromachining, or other processes. For example, this technique could be used to manufacture a mesh with stainless steel-based microhooks and Nitinol based cross bridges.

A range of fabrication techniques can be used to create microhooks or arrays of microhooks described herein. For example, microhooks can be designed and patterned on 2D substrates, and then bent or formed out of plane to create a 3D structure. Bending of needles can take place in two general schemes. The microhook can be pushed out of the plane of 2D material with the main displacement along its flatter edge in something like a trap-door. This method or microhook bending allows tunable angles set by a jig. The microhooks may provide low hold strength as this is dependent on the mechanical properties of the mesh material such at the Young's Modulus and dimensions. Conversely, a weak point can be engineered into the design so that high tensions on the microhooks allow them to bend out of the way and reduce stress and damage at the repair side. The microhook can also be rotated out of the plane of a 2D material in something like a shark fin rolling out of the water. This technique may maximize holding force but needles may rotate out of the way instead of penetrating into the repair tissue.

For example, a stainless steel sheet can be micro machined with a laser to cut out the outline of microhooks. These microhooks could then be bent out of plane using manual tools and techniques, or a customized jig.

Electron Discharge Machining (EDM) is another example of a manufacturing technique that can be used on a metal substrate. EDM could be used to make custom stamping jigs to fabricate the microhooks from sheet material and/or bend the needles out of plane automatically.

Manufacturing methods suitable for high volume manufacturing can be selected. For example, Photo Chemical Milling (PCM) is an established technique used to etch large metallic sheets and to fabricate precision metallic parts. PCM can offer varied thicknesses at strategic portions of the construct. For example, the front-side and back-side can both be etched to provide sections of half thickness. Motivations for varied thicknesses are described above.

Electropolishing or acid pickling techniques are other examples to smooth and/or thin portions of the device. For example, microhook tips can be electropolished for sharpness. The frame (e.g., planar base 100 of FIG. 1 and/or cross bridges 150 of FIGS. 4A and 4B) can be electropolished to thin it, clean it, or remove debris.

At production level, methodologies to manufacture microhook array meshes cost effectively can be developed. For example, large-area compatible photochemical milling (PCM) processes can be used for precise yet scalable microhook mesh fabrication. In addition, a custom stamping tool can also be developed for production scale translation of microhooks from 2D to 3D at specified angles. Adhesive examples: As described herein, the device for repairing a nerve (e.g., the device of FIGS. 1, 4A, 4B, 10A, 10B, and/or 11A-11C) can include a tissue adhesive. Cyanoacrylates, fibrin glues, protein applied and denatured by laser or UV light, carbohydrates, hydrogels, cellulose, or waxes are non-limiting examples of tissue adhesives. A variety of materials can be used as adhesive or tissue adhesive components to supplement or replace the mechanical attachment of the microhooks, to help entubulated the repair site, create an isolated environment at the repair site, promote tissue viability, or promote the pro-regenerative environment of the repair site.

Flexible Substrate or Backing Material

As described herein, the device for repairing a nerve (e.g., the device of FIGS. 1, 4A, 4B, 10A, 10B, and/or 11A-11C) can include a flexible substrate (e.g., flexible substrate 200 of FIG. 1, 6 or 7 or flexible carrier layer 625 of FIGS. 10A-11C). For example, the support member (e.g., planar base 100 of FIG. 1 or metallic support member 100 of FIGS. 4A-4B or metallic support member 600 of FIGS. 10A-11C) can be attached to the flexible substrate. As described herein, the micro-protrusions can form an array of micro-protrusions, where each of the micro-protrusions is independent. In this implementation, the flexible substrate, which is the backing material, provides mechanical strength and/or flexibility. Alternatively, the micro-protrusions can form an array of micro-protrusions, where each of the micro-protrusions is interconnected, e.g., by intersecting cross bridges (e.g., FIGS. 4A-4B) or elongate members (e.g., FIGS. 11A-11C). In this implementation, both the support member and the flexible substrate, which is the backing material, provide mechanical strength and/or flexibility. In other words, this disclosure contemplates that the combination of the support member and the backing material provide the mechanical strength and/or flexibility of the device. Neither the support member nor the backing material alone provide the needed mechanical strength and flexibility. The backing material can aid in isolation of the repair site. For example, the backing material can be folded over or wrapped around the repair site. Alternatively, multiple layers of the backing material can be "sandwiched" on other side of the repair site to provide isolation. Although the term backer or backing material is used, this is meant to loosely define the concept of microhooks being incorporated into any substrate separate from the microhooks themselves. For example, a microhook mesh can be laminated between two pieces of material before implantation. In another example, a microhook mesh can be wrapped around two severed nerve ends, and then the repair site can be further wrapped in a second material wrap, such as an SIS sheet. Or, an SIS tube can be pushed up one nerve stump, the two nerve stumps coapted with a microhook mesh, and then the SIS tube pulled over the repair site. Or, in another example, the two nerve stumps can be coapted with the microhook mesh, and then a tissue adhesive such as fibrin glue applied to the entire repair site, to form a protective clot and pro-regenerative environment. The microhooks may be applied as individual vertical bridges instead of a mesh, or as several vertical bridges applied at a time.

In some embodiments, the microhook mesh can provide the bulk of the mesh+backing material construct's mechanical/tensile strength. For example, a metallic lattice can be made very strong and resistant to the normal forces that the construct can be subjected to during and after implantation. The backing material in this case can serve primarily to selectively isolate the repair site, guiding and constraining regeneration and preventing the infiltration of fibroblasts or scar tissue. The backing material can isolate most of the lattice, such that body tissues interface primarily with the backing materials, except at the locations of the protruding microhooks.

In other embodiments, the backing material and the integrated microhook mesh can share any encountered forces. For example, the backing material can supplement the tensile strength of the microhook construct. As an example, the microhook mesh can be a lattice where the "horizontal" cross bridges have been reduced, thinned, or even eliminated. The backing material would then provide lateral support for the vertical cross bridges interconnecting of the microhooks.

In some embodiments, the backing material can contribute even more significantly to the overall strength of the device. For example, individual or small groups of microhooks can be distributed in isolated fashion within a backing material substrate. The backing material in this case bears the full tension of nerve repair. The base of each microhooks is adequately supported, such that the microhook is able to maintain its structure during penetration and in the face of tissue tension thereafter.

The backing material can be selected with the goal of promoting wound healing or tissue regeneration. For example, the backing material can be designed to isolate the repair site, keeping out infiltrating fibroblasts or scar tissues. The material can be selected to have pores of appropriate size to allow biochemical agents to still pass through the backing material.

The backing material can be on one or both sides of the microhooks or microhook mesh. One material can be used on one side of the mesh and another material used on the other side. For example, on the side of the construct that touches or faces the nerve, a very thin, or absence of, substrate can be used, to minimize the material between the nerve and microhooks. Microhooks can also be made longer to compensate for the thickness of this interior substrate layer. This interior substrate layer can also be chosen to have desired properties in regards to biocompatibility with the nerve tissue to in regards to promoting or influence regeneration of the nerve. The exterior side of the mesh can be a thicker substrate, for example. A thicker substrate can have more mechanical strength or resistance to crushing or kinking or other forces, or can provide more optimal entubulation or isolation of the repair site. One layer can be biodegradable such as PLLA/PLGA and another layer bioresorbable, such as processed porcine small intestinal submucosa (SIS) or collagen. Processed SIS and collagen are examples of extracellular matrix (ECM) scaffolds that can be infiltrated and gradually remodeled by native cells, leaving behind organized tissue.

The exterior layer can be designed with other properties, such as easy mechanical attachment via hooks, to provide a closure mechanism.

Another design goal of the backing material can be to allow some level of transparency through the device to aid in the implantation process.

The backing material can be involved in adhering to a bioadhesive or providing bioadhesive properties itself. For example, a combination of a biological inert and bioabsorbable backing (such as multi laminar porcine extracellular matrix sheet combined with a biologically inert, hydroresistant, tissue adhesive and mechanical microhooks can effectively and permanently co-apt severed nerve stumps and support axonal regeneration. For example, the backing material can be composed of a porcine intestine submucosa extracellular matrix (currently commercially available). There can be a "sticky" component to the microhook nerve tape, which can act as the closure mechanism.

For a backing material porcine small intestine submucosa (SIS) extracellular matrix (Cook Medical of Bloomington, IN). Porcine SIS has been demonstrated as a pro-regenerative material, able to patch and protect healing tissues, while not eliciting any additional inflammatory response. While often used independently, as an implant, porcine SIS material can be used in combination with a microhook mesh. In this case, the microhook mesh provides tensile strength that reinforces the flexible porcine SIS entubulation. The resulting bio-synthetic hybrid device can be efficiently applied to a severed nerve, coapting and entubulating the site, without the need for an expensive and bulky operating microscope.

Porous, biodegradable substrates can be suitable for long-term implantation and nerve entubulation. Porcine SIS is currently distributed as a conduit or wrap used in nerve repair or as a scar barrier, providing not just a substrate for microhooks, but a pro-regenerative microenvironment.

Specialized lamination processes can be used for reliable and scalable embedding of microhook meshes within porcine SIS. Microhook mesh can be laminated within multiple layers of porcine SIS. This process can involve a variety of lamination temperatures, pressures, and pore sizes for the microhook mesh construct. This process can be evaluated by using both the biomechanical and biological properties of the device. An appropriate lamination can be translated into a process with scalable manufacturing levels to produce a cost effective device.

Figure 5:
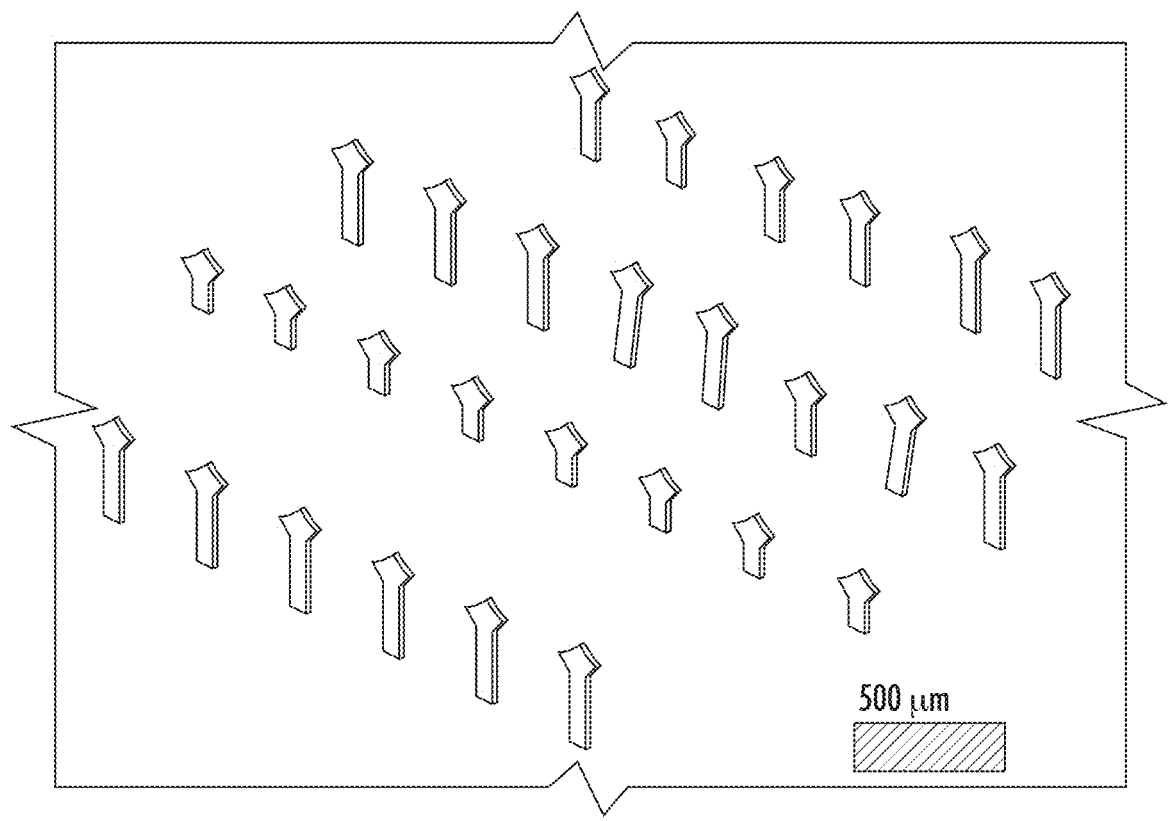
FIG. 5 illustrates another example device for repairing a nerve where a microhook mesh is embedded between layers of small intestine submucosa (SIS).

SIS sheets can be laminated directly together to form robust, multilayered substrates. In some implementations, a metallic microhook mesh can be embedded between SIS layers as shown in FIG. 5, which may block layer-to-layer bonding of the SIS layer, introducing the possibility of delamination. This delamination can be mitigated by increasing the number and size of the openings in the metallic mesh, allowing more surface area for SIS-to-SIS bonding. It should be understood that other biodegradable materials, including Poly Lactic Acid (PLA) and Poly Lactic-co-Glycolic Acid (PLGA) in case of issues with integrating of SIS with mesh structures can be used.

Closure Mechanism

As described herein, microhook meshes (e.g., planar base 100 including a plurality of micro-protrusions 110 of FIG. 1 and/or support members including a plurality of micro-protrusions as shown in FIGS. 4A-4B, 10A-10B, and 11A-11C) can be positioned to cover, and in some implementations wrap around, the nerve repair site. Thus, the microhook meshes can be configured to close in order to maintain entubulation around the repair site, e.g., coapted nerve ends. Ease of application is a goal of this design, and therefore, it is desirable that the closure mechanism be quick and simple, without requiring additional tools. Thus, in some implementations, the nerve repair device can include a fastener (also referred to herein as a mechanism for closure or closure mechanism) for maintaining entubulation and/or sandwiching of the repair site. The closure mechanism can include, but is not limited to, providing a microhook nerve tape having a unique shape (e.g., having tapered edges, triangular, trapezoidal, etc.) to allow self-closure when the wrap is complete, using two different materials in the backing—with an area of outer material that the microhooks can grab (i.e., the microhooks will not grab the regular backing material, and/or using an adhesive.

There are many possible mechanisms for closure, including, but not limited to, microhooks and backing material designed such that microhooks penetrate into the outside layer of backing material and then resist pulling out. Referring now to FIGS. 6-8, for example, the device can include longer fastening hooks 300 on the edge of the device, which are designed to penetrate and attach to underlying layers of the flexible substrate 200 as it is overlapped and wrapped. Specialized hooks on one edge of the microhook nerve tape, can be optimized for grabbing a modified back surface of the embedding substrate itself. Specialized needles could also interface with the embedded mesh structure and lock into place. Alternatively, complimentary loops or hook (e.g., hook and loop type fasteners 400A and 400B of Fig. *) could bind along the edge helping the wrap maintain closure.

Referring now to FIG. 6, an example nerve repair device, where the micro-protrusions 110 can attach to the nerve 120 and longer fastening hooks 300 separately attach to the flexible substrate 200 itself after wrapping, sandwiching, etc. is shown. In FIG. 6, the nerve repair device is wrapped around the nerve 120. The longer fastening hooks 300 are distributed along one edge of the planar base 100. When the device is wrapped around the nerve 120, the longer fastening hooks 300 penetrate or fasten to the flexible substrate 200 itself to provide a closure mechanism.

The device can be designed to remain closed partly due to the binding of microhooks to tissue. For example, in some implementations, the device can be designed such that one or more edges are tapered, for example, in the shape of a triangle or trapezoid, so that with each wrap around the tissue (e.g. nerve) more of the device comes in mechanical contact with new tissue. The point of the triangle (or smaller base of the trapezoid) can be arranged at the center of the repair site, and as the microhook nerve tape is wrapped, the triangle (or trapezoid) becomes wider and more microhooks engage into the nerve and hold the device shut.

In other implementations, the fastener can be, but is not limited to, staples, hooks, hook and loop type fasteners, crimps, adhesives, clasps, ties, sutures, zip-tie-like mechanisms, or a variety of other mechanical closure mechanisms. The microhook nerve tape may have a loop in end like a zip-tie or belt where the other end is threaded through. As tension is applied, the microhook nerve tape can lock into place. Key and slot and twist mechanisms can be used to lock the microhook nerve tape onto the repair tissue.

In other implementations, the fastener can be adhesives or bonding agents, which can aid in closure of the device. These adhesives can be activated by a variety of mechanisms, including time, heat, UV, chemical accelerators, multi-component compositions, moisture, proteins, or other enzymes.

The microhook nerve tape can have a natural conformation that it will return to. For example, a tube with a slit can be opened to accept the nerve ends, and then will naturally reclose by its own inherent tension. The microhook nerve tape can have a natural curl or wrap that it will roll back up into after being unrolled or flattened.

Specialized materials with shape memory and/or super-elastic properties, such as nickel-titanium (Nitinol) alloys can be used. When introduced into or near the body, these materials can change temperature to change shape. This change in conformation can cause bending, wrapping, movement of microhooks, entubulation, or other motion beneficial for tissue attachment and closure.

In some embodiments, the microhook nerve tape may not need a mechanism of closure. For example, the microhook nerve tape can be created from an intact tube, in which severed nerve ends can be insert into each end.

Referring now to FIGS. 7 and 8, two or more pieces of microhook nerve tape can be sandwiched on top of each other with mechanical or adhesive means of attachment/closure. FIG. 7 illustrates another example nerve repair device, wherein the micro-protrusions 110 can attach to the nerve 120 and longer fastening hooks 300 separately attach to the flexible substrate 200 itself after wrapping, sandwiching, etc. In FIG. 7, a plurality of nerve repair devices (e.g., two devices) are used to sandwich the nerve 120. The longer fastening hooks 300 are distributed along one edge of each of the planar bases 100. When the devices sandwich the nerve 120, the longer fastening hooks 300 penetrate or fasten to the respective flexible substrates 200 to provide a closure mechanism. It should be understood that the nerve repair device of FIG. 7 can be flexible although it is shown in FIG. 7 as being flat only as an example.

FIG. 8 illustrates another example nerve repair device, wherein the micro-protrusions 110 can attach to the nerve 120 and hook and loop type fasteners 400A, 400B are used to close the device after wrapping, sandwiching, etc. In FIG. 8, a plurality of nerve repair devices (e.g., two devices) are used to sandwich the nerve 120. The hook and loop type fasteners 400A, 400B are distributed along one edge of each of the planar bases 100. When the devices sandwich the nerve 120, the I hook and loop type fasteners 400A, 400B engage with each other to provide a closure mechanism. It should be understood that the nerve repair device of FIG. 8 can be flexible although it is shown in FIG. 8 as being flat only as an example.

Tools to Aid in Applying the Microhook Nerve Tape

A variety of specialized tools, jigs, or guides, can be used for aiding with the implantation and/or closure of the microhook nerve tape. For example, an alignment device with a base portion can accept the microhook nerve tape and keep it properly positioned and unfurled in the repair site. After wrapping of the microhook nerve tape, a second portion of the alignment device can depress to crimp or close the microhook nerve tape, creating an entubulated or sandwiched repair site. The alignment device can also assist in guiding the placement, alignment, or wrapping of the nerve. The alignment device can aid in the entubulation, closure, or sandwiching of the repair site.

A specialized tool can also temporarily attach to both transected ends. This tool can allow axial rotation of nerve ends to align internal fascicles before bringing the two ends together. Once together, this tool can apply nerve tape by either wrapping or sandwiching the nerve ends in microhook nerve tape. This tool can also fix the microhook nerve tape in place.

Another specialized tool can be used to assist in repositioning the microhook nerve tape. If, during the use of the microhook nerve tape, it is necessary to reposition the microhook nerve tape, a tool could be used to dis-engage the microhook nerve tape from tissue while causing minimal disruption to tissue and preserving the integrity of the device.

Another specialized tool can also be designed so that a triangular or trapezoidal microhook nerve tape can be wrapped around the transected nerve multiple times. This tool can grab both ends of a nerve, align the ends and bring them together. Then a pre-loaded microhook nerve tape piece can be automatically wrapped around the repair site, self-locking in place.

Two Piece Nerve Tape

In some implementations, microhook nerve tape can include a plurality of pieces of materials, e.g., two pieces of material. Although two and three piece nerve tape are described as examples, it should be understood that the microhook nerve tape can include more than three pieces of material. Each piece can independently attach to a nerve end. The ends can then be brought together, aligned, and fastened using a variety of fastening mechanisms, including interlocking clasps, posts and loops, slots and keys, or some sort of meshing. Alternatively, the two pieces can be attached at one point along their circumference and left open to allow alignment. Once aligned and engaged into the tissues, the two pieces can be closed like a book and locked together. After the physical attachments have been made, a piece of SIS or other entubulation material can be slid over the repair site. This can be locked into place easily with a locking mechanism on the nerve tape. Optionally, the mechanical aspects of nerve tape may be made from bio-absorbable polymers, so that in 2-3 months, the mechanical elements have dissolved and left a repaired nerve entubulated in SIS.

Three Piece Nerve Tape

Nerve tape can also be a three part system. Two pieces of nerve tape can be applied to both ends of a cut nerve, respectively, and then brought together with a third piece (i.e., middle piece) of nerve tape. This third piece may vary depending on the attachment method chosen. In one example, the third piece may have threads on it. The threads could be spun onto each nerve end independently, bringing them together and aligning the ends on the process. Alternatively, the third piece may be spring loaded to control tension at the repair site. Alternatively, the third piece may have its length adjustable to accommodate different gaps. Alternatively, the third piece may attach to the needle pieces with hook and look, post and loop, key and slot or some other mechanism which securely locks everything in place.

Electrical Stimulation

This disclosure contemplates that the support member (e.g., planar base 100 of FIG. 1 or metallic support member 100 of FIGS. 4A-4B or metallic support member 600 of FIGS. 10A-11C) and/or the micro-protrusions (e.g., micro-protrusions 110 of FIGS. 1 and 4A-4B or micro-protrusions 610 of FIGS. 10A-11C) can be made of metallic or otherwise conductive materials, such as conductive polymer materials, to provide a means for electrical stimulation or recording. Electrical stimulation, for example, can be used as a means of promoting tissue repair, regeneration, or vascularization. Electrical stimulation of injured or regenerating nerves has been shown to promote or accelerate the repair/healing/regeneration process. Electrical stimulation of nerves or muscle can be used to maintain or promote muscle tone. Electrical stimulation can be used to stimulate response in target tissues such as organs, glands or muscles. Electrical recordings can be used to intercept bioelectrical signals from nerves or muscles, for example, as in the case of neural interfacing.

Drug Delivery/Cell Implantation

This disclosure contemplates that the nerve tape device described herein can also serve as scaffolds for drug delivery or cell transplantation. Thus, the nerve tape device described herein may offer a useful platform for the delivery of nerve regeneration enhancing agents including growth factors and future pharmaceutical treatments.

Results

As described herein, devices for repairing a nerve (also sometimes referred to as "nerve tape") are described herein. Prototypes of various nerve repair devices have been tested as described below. In controlled experiments, the resulting stainless steel-based prototypes were comparable in holding strength to conventional suture repairs. Implantation of the devices around intact rabbit nerves for 1 and 3 months suggested no adverse tissue response as compared to microsutures. In four-month nerve repair experiments, nerve regeneration in the microhook nerve tape group was not significantly different from microsuture group, as gauged by outcome metrics of reinnervated muscle weight, nerve conduction, and histomorphometry.

Despite the overall positive performance, stainless steel-based prototypes were found to exhibit "crimping" if not carefully applied. For example, the crossbars (e.g., one or more cross bridges 150A, 150B shown in FIGS. 4A-4B) of the stainless steel mesh can slightly "crimp" as it wraps around the nerve, leading to potential constriction. As demonstrated with proof-of-concept devices, "crimping" can be eliminated by a design modification (e.g., using a Nitinol mesh, without crossbars such as the device shown in FIGS. 11A-11C).

A series of candidate metals were laser cut for evaluation, including stainless steel 316L, Nitinol, titanium, platinum iridium, and biodegradable alloys of magnesium and iron. Stainless steel was selected as the primary candidate for initial testing, based on its mechanical strength, ability to manually bend microhooks out of plane, and an established track record of tolerability around nerves. Nitinol exhibited excellent properties as well, but was initially selected as an alternate material, based on the need for specialized tooling for microhook bending. Biodegradable alloys demonstrated suboptimal mechanical characteristics, and polymer-based materials were similarly ruled out due to lack of necessary materials properties (e.g. strength, hardness) to penetrate and hold epineurial tissue.

Metal thickness, microhook geometries, and array parameters were tuned through over a dozen iteration cycles informed by quantitative biomechanical testing on human cadaver nerves. Resulting example microhook parameters are shown in Table 4 below. Design parameters emphasized minimizing invasiveness while maximizing strength and flexibility. For example, microhook lengths were varied in 25 µm steps to identify the minimum length required to extend through the SIS material and reliably engage and hold epineurial tissue. Crossbar (e.g., cross bridges 150A, 150B shown in FIGS. 4A-4B and/or elongate strips 650 shown in FIGS. 11A-11C) counts and widths were manipulated to maximize mesh flexibility while retaining sufficient microhook support.

TABLE 4

| Microhook parameter | Tested range | Selected Value |
| --- | --- | --- |
| Shank length | 100-800 μm | 425 μm |
| Shank width | 75-150 μm | 200 μm |
| Microhook count | 16-64 hooks | 32 hooks |
| Array density | 1-2 mm$^2$ pitch | 1.5 mm$^2$ |
| Metal thickness | 25-100 μm | 50 μm |
| Microhook angle | 30° to 60° | 40° |
| Mesh row width | 50-150 μm | 150 μm |
| Mesh column width | 50-150 μm | 150 μm |
| Crossbar density | 12.5-100% | 40% |

Other design characteristics were developed to improve device performance. For example, microhook architecture was altered such that, microhooks were rotated laterally out of plane along an axis normal to applied nerve tension (e.g., as shown in FIG. 4B). This configuration increased hook strength, allowed a precise and consistent bending angle (since this angle is patterned into the 2D layout), and resulted in a safer design where the microhook does not penetrate deeper into the nerve during increased loading.

Several candidate backing materials were evaluated (e.g. biologics such as collagen and SIS, and biodegradable polymers). Porcine small intestinal submucosa (SIS) sheets was selected, based on its excellent mechanical properties, biointegration (e.g., provides an extra cellular matrix for ingrowth and repopulation with native tissue), and well-established use as an FDA-approved clinical nerve wrap. SIS parameters such as layer count and pre-processing techniques were varied, and protocols of mesh placement, lamination, and sterilization were developed. Both the SIS itself and also the attachment strength between the SIS and laminated microhook meshes were extremely robust in bearing tension.

Candidate microhook meshes were evaluated throughout development in benchtop testing with both human and rabbit cadaver nerves to investigate penetration profiles. Microhooks extending within an appropriate window of penetration length (normal to the substrate) were observed to penetrate and affix only the superficial nerve layers.

Figure 12:
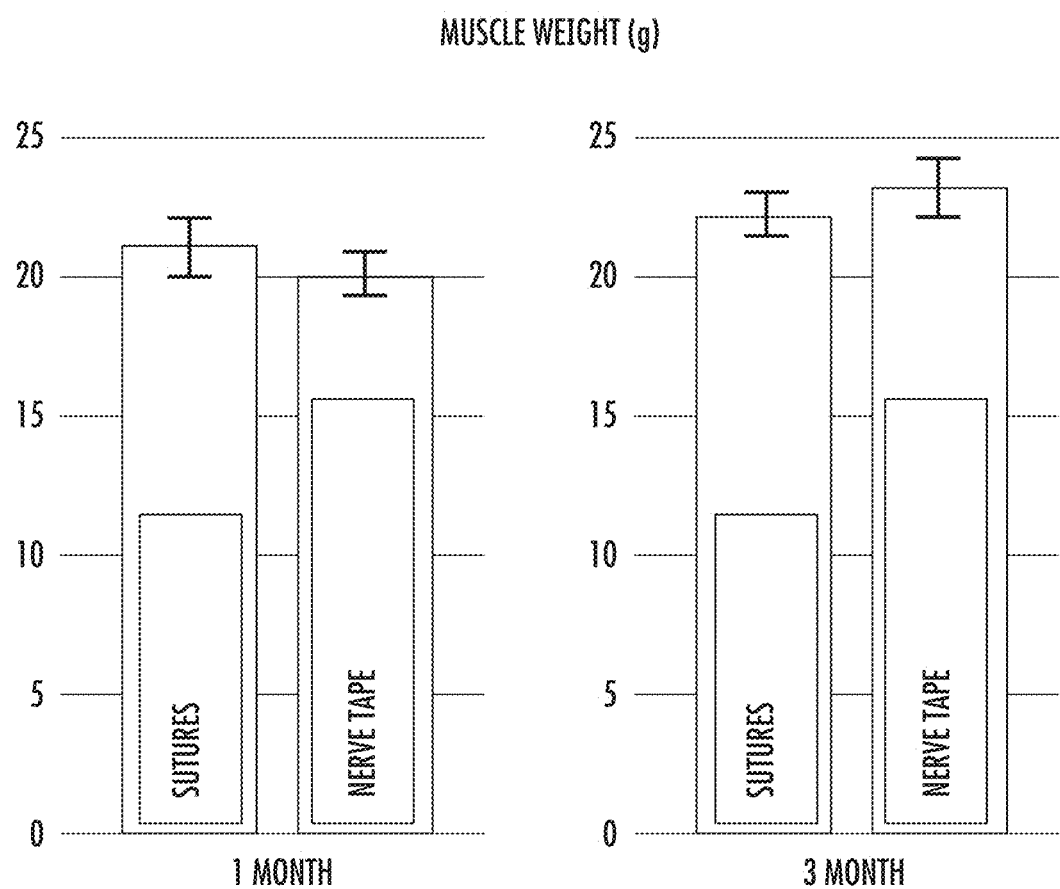
FIG. 12 are graphs illustrating gastrocnemius muscle weight at 1 and 3 months, respectively, for conventional sutures (i.e., "sutures" in FIG. 12) and a nerve repair device according to an implementation described herein (i.e., "nerve tape" in FIG. 12).

Referring now to FIG. 12, graphs illustrating gastrocnemius muscle weight at 1 and 3 months, respectively, for conventional sutures (i.e., "sutures" in FIG. 12) and a nerve repair device according to an implementation described herein (i.e., "nerve tape" in FIG. 12) are shown. As a measure of chronic impact on nerve tissue, nerve tape devices were implanted around intact rabbit tibial nerves in comparison with four 9-0 nylon sutures. The nerve tape tested for FIG. 12 included a stainless steel support member having a plurality of micro-protrusions (e.g., microhooks). At 1-month and 3-month time points (N=4; 16 total rabbits) the nerves and muscles were explanted for histology and evaluated for tissue reactivity or direct nerve damage.

At the 1-month time point, gross inspection revealed increased encapsulation around the larger microhook nerve tape as compared to the suture repair site. At 3 months, however, a more definable tissue plane with much less inflammation surrounded the nerve tape site as compared to the earlier time point. Conversely, the suture group had more diffuse but moderate fibrotic tissue formation after three months. These observations suggest that the SIS material may have been remodeled, while the nylon had a persistent foreign body reaction. Similarly, muscle weight analysis suggested slightly lower muscle weights as shown in FIG. 12 in the nerve tape groups after 1 month, and at the 3-month time point, the differences were reversed. It should be understood that neither time point difference in FIG. 12 was statistically significant (N=4.) These results suggest no overt adverse tissue response or nerve damage caused by microhook nerve tape as compared to microsutures.

Figure 13A:
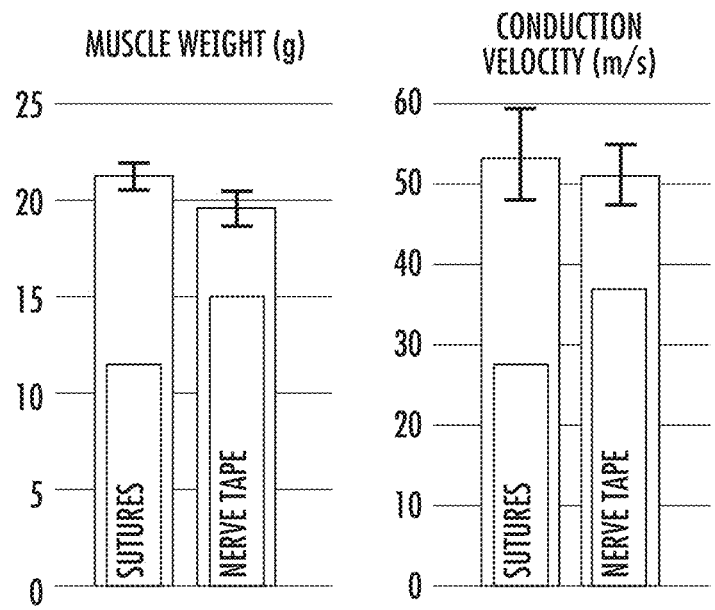
FIG. 13A are graphs illustrating rein nervated muscle weight and nerve conduction velocity for conventional sutures (i.e., "sutures" in FIG. 13A) and a nerve repair device according to an implementation described herein (i.e., "nerve tape" in FIG. 13A).
Figure 13B:
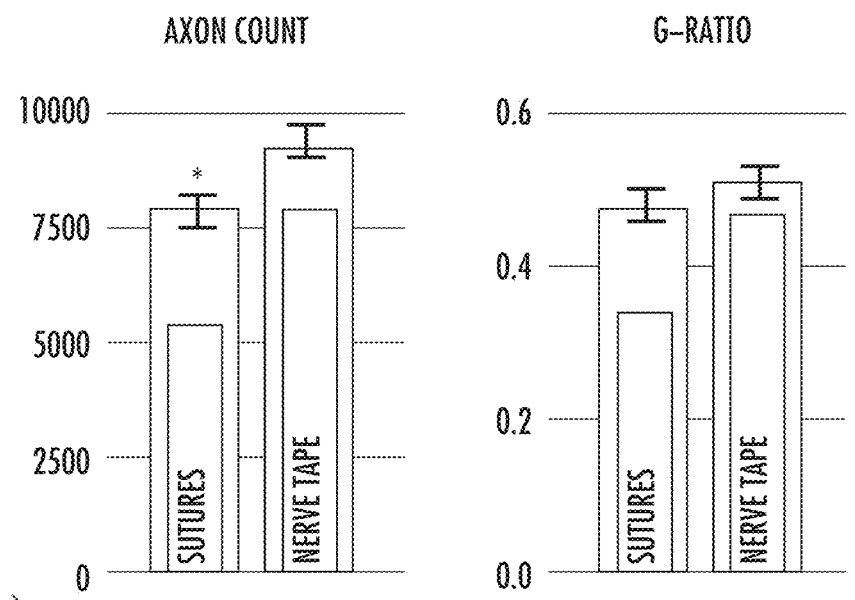
FIG. 13B are graphs illustrating axon count and G-ratio (e.g., histomorphology measures) for conventional sutures (i.e., "sutures" in FIG. 13B) and a nerve repair device according to an implementation described herein (i.e., "nerve tape" in FIG. 13B).

Referring now to FIGS. 13A and 13B, graphs illustrating results of nerve conduction studies are shown. FIG. 13A illustrates rein nervated muscle weight and nerve conduction velocity for conventional sutures (i.e., "sutures" in FIG. 13A) and a nerve repair device according to an implementation described herein (i.e., "nerve tape" in FIG. 13A). FIG. 13B illustrates axon count and G-ratio (e.g., histomorphology measures) for conventional sutures (i.e., "sutures" in FIG. 13B) and a nerve repair device according to an implementation described herein (i.e., "nerve tape" in FIG. 13B). The nerve tape tested for FIGS. 13A-13B included a stainless steel support member having a plurality of micro-protrusions (e.g., microhooks).

In 20 rabbits, the tibial nerve was transected and repaired with either sutures or microhook nerve tape (N=10), and regeneration was assessed after four months. Visual inspection by the surgeon during nerve explant and microhook nerve tape unwrapping did not reveal gross differences in scarring, and there was no evidence of mechanical repair failure in any animal. Nerve conduction studies revealed similar conduction velocities between groups (measured by onset of the compound action potential). Reinnervated muscle weights (gastrocnemius) were higher in suture groups, though differences were not statistically significant (p=0.14). Finally, blinded analysis of radially sectioned nerve (5 mm distal to the repair site) demonstrated no statistically significant differences in average axon diameter, myelin thickness, or G-ratio. Axon counts were significantly higher in sections nerve tape sections (p=0.03).

Safety testing on intact nerves suggested that when microhook nerve tape is carefully applied, associated morbidity is not significantly higher than with conventional microsutures. In efficacy testing (e.g., results shown in FIGS. 12, 13A, and 13B), the nerve tape prototypes maintained similar attachment strength and supported a level of nerve regeneration not found to be significantly different from microsuture repairs.

As discussed above, faulty wrapping can result in a "crimping" effect that constricts the nerve and reduces functional outcomes (e.g. muscle weight). This effect can be minimized or eliminated with careful application techniques and/or providing microhook nerve tape as a clinical device that is simple and risk-free to apply. Alternatively or additionally, this effect can be minimized or eliminated by using Nitinol support members (e.g., as shown in FIGS. 11A-11C).

Figure 14:
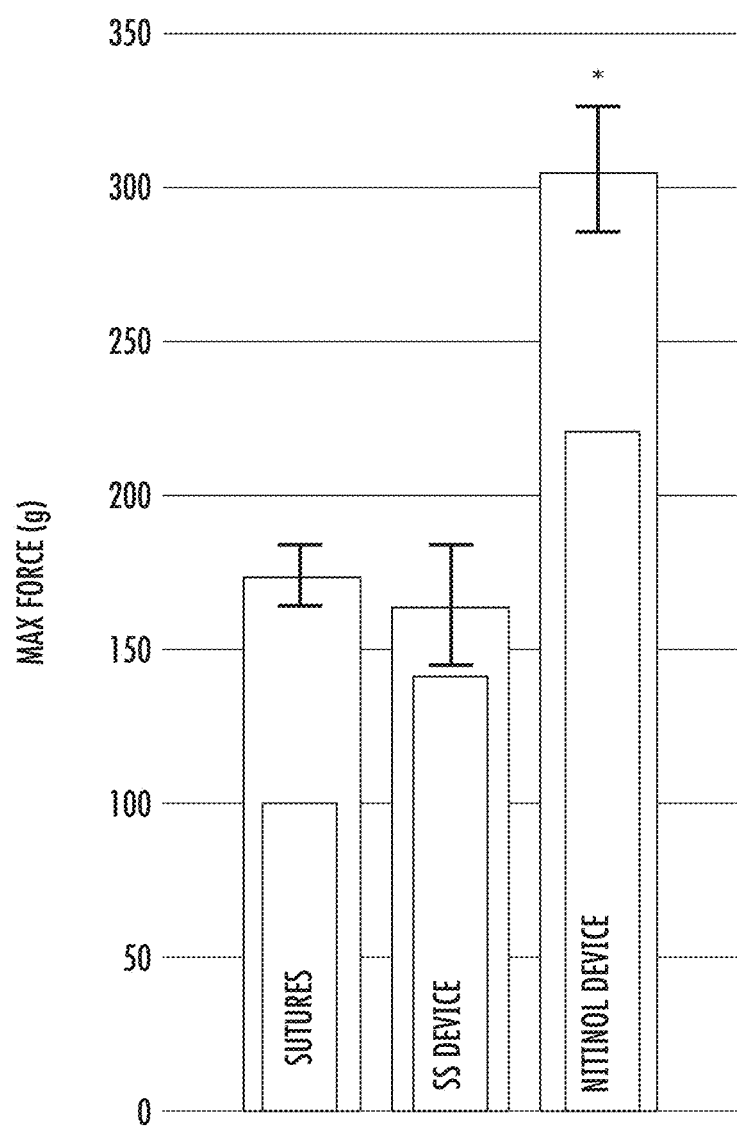
FIG. 14 is a graph illustrating attachment force for conventional sutures (i.e., "sutures" in FIG. 14), a nerve repair device according to an implementation described herein (i.e., "nerve tape" in FIG. 14), and a Nitinol nerve repair device according to an implementation described herein (i.e., "Nitinol prototype" in FIG. 14).

Referring now to FIG. 14, a graph illustrating attachment force for conventional sutures (i.e., "sutures" in FIG. 14), a nerve repair device according to an implementation described herein (i.e., stainless steel "SS device" in FIG. 14), and a Nitinol nerve repair device according to an implementation described herein (i.e., "Nitinol device" in FIG. 14) is shown. In FIG. 14, the SS device tested included a stainless steel support member having a plurality of micro-protrusions (e.g., microhooks), and the Nitinol device included a Nitinol support member having a plurality of micro-protrusions (e.g., microhooks). The Nitinol prototype's properties allowed it to withstand lamination even with disconnection of horizontal crossbars. Because the disconnected Nitinol strips (e.g., elongate strips 650 shown in FIG. 11A) "float" within the conformable SIS (e.g., as shown in FIGS. 11A-11C), this design eliminates possible crimping or constriction. Resistance to nerve wrapping is also removed, and the SIS/Nitinol construct closely contoured nerve ends. As a result, microhook engagement was markedly improved, and biomechanical testing confirmed improved holding strength as compared to both stainless steel prototypes and microsutures as shown in FIG. 14. Additionally, the properties of Nitinol allowed removal of material that resisted wrapping without loss of stability, and microhooks can also be shortened, which is a by-product of the forming process. Thus, the Nitinol device is by nature less invasive and provides stronger attachment.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A device, comprising:
   a flexible carrier layer; and
   a support member comprising a plurality of elongate strips and a plurality of micro-protrusions, the micro-protrusions extending from the elongate strips, wherein:
   the support member is at least partially integrated with the flexible carrier layer,
   the support member is formed of a first material,
   the flexible carrier layer is formed of a second material that is different than the first material,
   the flexible carrier layer is configured to cover at least a portion of a tissue,
   the micro-protrusions are configured to mechanically interface with the tissue,
   the micro-protrusions comprise a first group of micro-protrusions and a second group of micro-protrusions,
   the elongate strips are not interconnected with one another within the flexible carrier layer,
   the elongate strips are configured to extend across a repair site of the tissue, and
   the first group of micro-protrusions and the second group of micro-protrusions are oriented in opposite directions and configured to apply a holding force at the repair site of the tissue.

2. The device of claim 1, wherein, for each of the elongate strips, a respective length extending along a first axis is longer than a respective length extending along a second axis, wherein the first axis extends across the repair site of the tissue.

3. The device of claim 2, wherein the micro-protrusions are bent out of plane with respect to the support member in a direction of the first axis or the second axis.

4. The device of claim 3, wherein the micro-protrusions are bent out of plane with respect to the support member in the direction of the first axis.

5. The device of claim 3, wherein the micro-protrusions are bent out of plane with respect to the support member in the direction of the second axis, and wherein the second axis is substantially perpendicular to the first axis.

6. The device of claim 1, wherein the first and second groups of micro-protrusions are oriented to face each other.

7. The device of claim 1, wherein each of the elongate strips further comprises one or more projecting members configured to stabilize the micro-protrusions within the flexible carrier layer.

8. The device of claim 1, wherein micro-protrusions are not provided along the elongate strips in a region of the support member.

9. The device of claim 1, wherein at least one of the flexible carrier layer or the support member is configured for drug delivery or cell transplantation.

10. The device of claim 1, wherein the micro-protrusions comprise at least one of micro-hooks or micro-needles.

11. The device of claim 1, wherein at least one of the micro-protrusions comprises a barb.

12. The device of claim 1, wherein at least one of the support member or the micro-protrusions is configured for delivering electrical stimulation or recording electrical activity.

13. The device of claim 1, wherein the device is configured for self-closure.

14. The device of claim 13, wherein the flexible carrier layer comprises a wrapping portion.

15. The device of claim 14, wherein the micro-protrusions are not arranged in the wrapping portion.

16. The device of claim 1, wherein the first material is a metal.

17. The device of claim 16, wherein the metal is a superelastic alloy.

18. The device of claim 17, wherein the superelastic alloy is of a composition that comprises nickel and titanium.

19. The device of claim 1, wherein the micro-protrusions are configured to attach to a superficial aspect of the tissue.

20. The device of claim 1, wherein the tissue is a nerve, and wherein the micro-protrusions are sized and shaped to pierce the outer epineurium of the nerve.

21. The device of claim 20, wherein the micro-protrusions are sized and shaped to not pierce a fascicle of the nerve.

22. The device of claim 1, wherein the second material is a biocompatible, biodegradable, or bioresorbable material.

23. The device of claim 1, wherein the second material is a biologic material.

24. The device of claim 23, wherein the biologic material is an extracellular material, small intestine submucosa (SIS), collagen, amniotic tissue, or chitosan.

25. The device of claim 1, wherein the flexible carrier layer is configured to cover at least the portion of the tissue, wherein the tissue is a nerve, a muscle, a tendon, or vasculature.

26. The device of claim 1, wherein the flexible carrier layer is a two-dimensional sheet.

27. The device of claim 26, wherein the flexible carrier layer is further configured to entubulate the repair site or sandwich the repair site.

28. A device for repairing a nerve, comprising:
   a flexible carrier layer; and
   a support member comprising a plurality of elongate strips and a plurality of micro-protrusions, the micro-protrusions extending from the elongate strips, wherein:
   the support member is at least partially integrated with the flexible carrier layer,
   the support member is formed of a first material,
   the flexible carrier layer is formed of a second material that is different than the first material,
   the flexible carrier layer is configured to cover at least a portion of the nerve, the micro-protrusions are configured to attach to a superficial tissue of the nerve, the micro-protrusions comprise a first group of micro-protrusions and a second group of micro-protrusions, the elongate strips are not interconnected with one another within the at least one flexible carrier layer, the elongate strips are configured to extend across a repair site of the nerve, and the first group of micro-protrusions and the second group of micro-protrusions are oriented in opposite directions and configured to apply a holding force at the repair site of the nerve.

* * * * *